(12) United States Patent
Berg

(10) Patent No.: US 7,176,294 B2
(45) Date of Patent: Feb. 13, 2007

(54) TRANSCRIPTION FACTOR, BP1

(75) Inventor: Patricia E. Berg, Accokeek, MD (US)

(73) Assignee: George Washington University, Washington, DC (US)

( * ) Notice: Subject to any disclaimer, the term of this patent is extended or adjusted under 35 U.S.C. 154(b) by 577 days.

(21) Appl. No.: 10/143,897

(22) Filed: May 14, 2002

(65) Prior Publication Data

US 2003/0171273 A1    Sep. 11, 2003

Related U.S. Application Data

(62) Division of application No. 09/636,735, filed on Aug. 11, 2000, now Pat. No. 6,416,956.

(60) Provisional application No. 60/148,940, filed on Aug. 13, 1999.

(51) Int. Cl.
*C07H 21/02* (2006.01)

(52) U.S. Cl. .............. 536/23.1; 536/24.33; 435/320.1; 435/325

(58) Field of Classification Search ............... 536/23.1, 536/234.5; 435/320.1, 69.1, 325
See application file for complete search history.

(56) References Cited

U.S. PATENT DOCUMENTS

| 5,677,125 A | 10/1997 | Holtz et al. |
| 5,700,927 A | 12/1997 | Zon et al. |
| 5,776,683 A | 7/1998 | Smith et al. |
| 5,965,409 A | 10/1999 | Pardee et al. |
| 5,981,218 A | 11/1999 | Rio et al. |
| 5,994,062 A | 11/1999 | Mulshine et al. |
| 6,004,756 A | 12/1999 | Watson et al. |
| 6,037,129 A | 3/2000 | Cole et al. |

OTHER PUBLICATIONS

Verma et al. (Nature 1997, 389: 239-242).*
Amalfitano et al. (Current Gene Therapy 2002, 2: 111-133).*
Pandha et al. (Current Opinion in Investigational Drugs 2000; 1 (1): 122-134).*
Chase et al., Mol Cell Biol. Apr. 2002;22(8):2505-14.*
Berg et al., Nucleic Acids Res. Nov. 11, 1989;17(21):8833-52.*
Berg, P.E., et al, Oncogenic potential of BP1/D1x9 in acute leukemia. Proc. Am. Assoc. Cancer Res. 40. 375, 1999.
Berg, P.E. et al, Overexpression of BP1/DLX9 in acute Myeloid Leukemia. Blood 92 Suppl 1(1) :603a 1998.
Fu S, et al, Mapping of a new homeobox gene, BP1, near its isoform DLX7 and characterization of their roles in repression of the beta globin gene. *Am. J. Hum. Gen. 1998*; 63: A181.
Berg P.E., et al, BP1, a new homeobox gene, is aberrantly expressed in acute leukemias, Blood, 90 Suppl. 1 (2) :209b 1997.
Berg, P.E., et al, Cloning of Beta Protein 1, a repressor of the human beta globin gene. Blood 88 suppl 1:472a, 1996.
Chase, M. B., S. Haga, W. D. Hankins, D. M. Williams, Z. Bi, J. W. Strovel, C. Obriecht, and P. E. Berg. 1999. Binding of HMG-I (Y) elicits structural changes in a silencer of the human β-globin gene. Am. J. Hem. 60: 27-35.
Berg, P.E., Ruscetti, R.W., Karp, J.E., Ross, D.D., Huguenin, S. and Haga, S. Aberrant expression of BP1, a new homeobox protein, in acute leukemia. Proc. Am. Assoc. Cancer Res. 39: 450, 1998.
Quinn, L. M., et al, 1997. Isolation and identification of homeobox genes from human placenta including a novel member of the Distal-less family, DLX4. Gene 187: 55-61.
Berg, P. E., D. M. Williams, R.-L. Qian, R. B. Cohen, S. X. Cao, M. Mittelman, and A. N. Schechter. 1989. A common protein binds to two silencers 5' to the human β-globin gene. Nucl. Acids Res. 17: 8833-8852.
Elion, J., P. E. Berg, C. Lapoumeroulie, G. Trabuchet, M. Mittelman, R. Krishnamoorthy, A. N. Schechter, and D. Labie. 1992. DNA sequence variation in a negative control region 5' to the β-globin gene correlates with the phenotypic expression of the $\beta^s$ mutation. Blood 79: 787-792.
Ebb, D., D. C. Tang, L. Drew, K. Chin, P. E. Berg, and G. P. Rodgers. 1998. Identification of regulatory elements that repress adult beta-like globin genes. Blood Cells, Mol., Dis. 24: 356-369.).
Price, J. A., D. W. Bowden, J. T. Wright, M. J. Pettenati, and T. C. Hart. 1998. Identification of a mutation in D1x3 associated with tricho-dento-osseous (TDO) syndrome. Hum. Mol. Gen. 7: 563-569).

(Continued)

*Primary Examiner*—Misook Yu
(74) *Attorney, Agent, or Firm*—Todd L. Juneau

(57) ABSTRACT

An isolated DNA of SEQ ID NO:1 is provided that encodes the transcription factor BP1, which is believed to be a repressor of the β-globin gene. A host cell that is transformed with a vector that contains the DNA may be used to produce BP1. Vectors having a controllable promoter operably connected to the BP1 open reading frame may be used to transform β-globin producing cells of patients with sickle cell anemia, thereby providing a treatment. Because BP1 is overexpressed in leukemia and breast cancer cells, acute myeloid leukemia, acute lymphocytic leukemia, and breast cancer can be screened for and diagnosed by determining whether BP1 is overexpressed in cell samples of patients who may have these conditions. An antisense DNA or RNA to the DNA encoding BP1 may be used as a treatment for acute myeloid leukemia, acute lymphocytic leukemia, and breast cancer.

6 Claims, 14 Drawing Sheets

OTHER PUBLICATIONS

Chebloune, Y., J. Pagnier, G. Trabuchet, C. Faure, G. Verdier, D. Labie, and V. M. Nigon. 1988. Structural analysis of the 5' flanking region of the β-globin gene in African sickle cell anemia patients: further evidence for three origins of the sickle cell mutation in Africa. Proc. Natl. Acad. Sci. USA 85: 4431-4435).

Berg, P. E., M. Mittelman, J. Elion, D. Labie, and A. N. Schechter. 1991. Increased protein binding to a -530 mutation of the human β-globin gene associated with decreased β-globin synthesis. Am. J. Hematol. 36: 42-47.

Look A. T., Oncogenic transcription factors in the human acute leukemias. *Science* 1997; 278: 1059-1064.).

Zeng, F.-y., G. P. Rodgers, S.-z. Huang, A. N. Schechter, M. Salamah, S. Perrine, and P. E. Berg. 1994. Sequence of the -530 region of the beta globin gene of sickle cell anemia patients with the Arabian haplotype. Human Mutation 3: 163-165).

van Oostveen JW, Biji JJ, Raaphorst FM, Walbooners JJM, Meijer CJLM. The role of homeobox genes in normal hematopoiesis and hematological malignancies. *Leukemia* 1999; 13: 1675-1690.

Simeone A, Acampora D, Pannese M, D'Esposito M, Stornaiuolo A, Gulisano M, Mallamaci A, Kastury K, Druck T, Huebner K. Cloning and characterization of two members of the vertebrate D1x gene family. *Proc Natl Acad Sci USA* 1994; 91: 2250-2254.).

Shen W-F, Largman C, Lowney P, Corral JC, Detmer K, Hauser CA, Simonitch TA, Hack FM, Lawrence HJ. Lineage-restricted expression of homeobox-containing genes in human hematopoetic cell lines.

Database Genbank, Accession No. U73328, Nakamura et al Genomic Analysis of a New Mammalian distal-less Gene: KLx7. Gene Sequence. Genomics. 1996, vol. 38, No. 3 pp. 314-316.

Shimamoto, T., S. Nakamura, J. Bollekens, F. H. Ruddle and K. Takeshita. 1997. Inhibition of Dlx-7 homeobox gene causes decreased expression of GATA-1 and c-myc genes and apoptosis. Proc. Natl. Acad. Sci. USA 94: 3245-3249).

* cited by examiner

FIG. 4

```
CCGCCCGGGC AGGTGGGAAC CGAACCCGAT GGAGAGGAGG GGGCCCCCAT GGATTTAGGG  60
GGGGAGGGGA AAGTCATGGG GGGGCACCCC CCCGGAACCC CTTTCCCAGG CGCGCGTTCT 120
CCGCTGAAAG AGGCTCAGAG AGACACTTTC TCCGGGATCT TAAGTGTGGG GGCTGCTGGC 180
TGGGGGGCCC GTCCGGCCCA ACGCCGGAGG CTTGCAAAAG AGAGTTAGCA GCGGGAGCGG 240
ACTACGTGCC GGGCCATGGC CCTTCTGCCC GGGCCCTGGC CACA                 284
```

```
ATGACCTCTTTGCCCTGCCCCCTCCCCGGCCGGGACGCCTCCAAAGCTGTCTTCCCAGACCTC 347
 M  T  S  L  P  C  P  L  P  G  R  D  A  S  K  A  V  F  P  D  L   (21)
```

```
GCCCCTGTCCCGTCGGTAGCGGCTGCCTACCCGCTTGGCTTGTCCCCTACAACCGCAGCCTCC 410
 A  P  V  P  S  V  A  A  A  Y  P  L  G  L  S  P  T  T  A  A  S   (42)
```

```
CCCAATTTGTCCTACTCCAGGCCGTATGGCCACCTCCTGTCTTACCCCTACACCGAGCCAGCG 473
 P  N  L  S  Y  S  R  P  Y  G  H  L  L  S  Y  P  Y  T  E  P  A   (63)
```

```
AACCCCGGAGACTCCTACCTGTCCTGCCAGCAACCCGCGGCGCTCTCTCAGCCCCTCTGCGGA 536
 N  P  G  D  S  Y  L  S  C  Q  Q  P  A  A  L  S  Q  P  L  C  G   (84)
```

```
CCTGCAGAGCACCCTCAGGAACTCGAGGCAGACTCGGAGAAGCCGCGGCTGTCCCCGGAACCC 599
 P  A  E  H  P  Q  E  L  E  A  D  S  E  K  P  R  L  S  P  E  P   (105)
```

```
TCCGAGCGGCGCCCTCAGGCCCCCGCCAAAAAGCTCCGCAAGCCGAGGACCATCTACTCCAGC 662
 S  E  R  R  P  Q  A  P  A  K  K  L  R  K  P  R  T  I  Y  S  S   (126)
```

```
CTGCAGCTGCAGCACCTAAACCAGCGTTTCCAGCACACGCAGTACCTGGCGCTGCCCGAGAGG 725
 L  Q  L  Q  H  L  N  Q  R  F  Q  H  T  Q  Y  L  A  L  P  E  R   (147)
         helix 1
```

```
GCCCAGCTGGCAGCGCAGCTCGGCCTCACCCAGACCCAGGTAAAGATCTGGTTTCAGAACAAA 788
 A  Q  L  A  A  Q  L  G  L  T  Q  T  Q  V  K  I  W  F  Q  N  K   (168)
         helix 2                    helix 3
```

```
CGCTCCAAGTATAAGAAGCTCCTGAAGCAGAATTCTGGGGGGCAGGAAGGGGACTTCCCTGGG 851
 R  S  K  Y  K  K  L  L  K  Q  N  S  G  G  Q  E  G  D  F  P  G   (189)
```

```
AGGACCTTCTCTGTGTCTCCCTGCTCCCCACCCCTCCCCTCCCTCTGGGATCTACCCAAGGCA 914
 R  T  F  S  V  S  P  C  S  P  P  L  P  S  L  W  D  L  P  K  A   (210)
```

```
GGGACCCTGCCCACCAGTGGCTATGGCAACAGCTTTGGAGCCTGGTATCAGCATCACTCCTCA 977
 G  T  L  P  T  S  G  Y  G  N  S  F  G  A  W  Y  Q  H  H  S  S   (231)
```

```
GATGTCCTGGCTTCGCCTCAGATGATG                                     1004
 D  V  L  A  S  P  Q  M  M                                       (240)
```

```
TGAATCTGGG GAAGGGCGGG TCAGGCCCAC AGCCTTCCTG CAAAGCCCAG GACCCAGGCA 1064
GTCCACCTGC ACCCCTTCTG GGCTGGGAGG AAACCAGCTC CAGATGGGTT TTCTCTGGAG 1124
GACAAACAGT TAGAGGAGAA AAAGGAATGG AGCAGAGCCT GTACCCCTAA CCCTAACAGC 1184
TAAATCAAGG ACCTCAGCCT TATATAATCA TTGTCCCCAC CACTACCATG GACTGAACAC 1244
CTTCACC                                                         1251
```

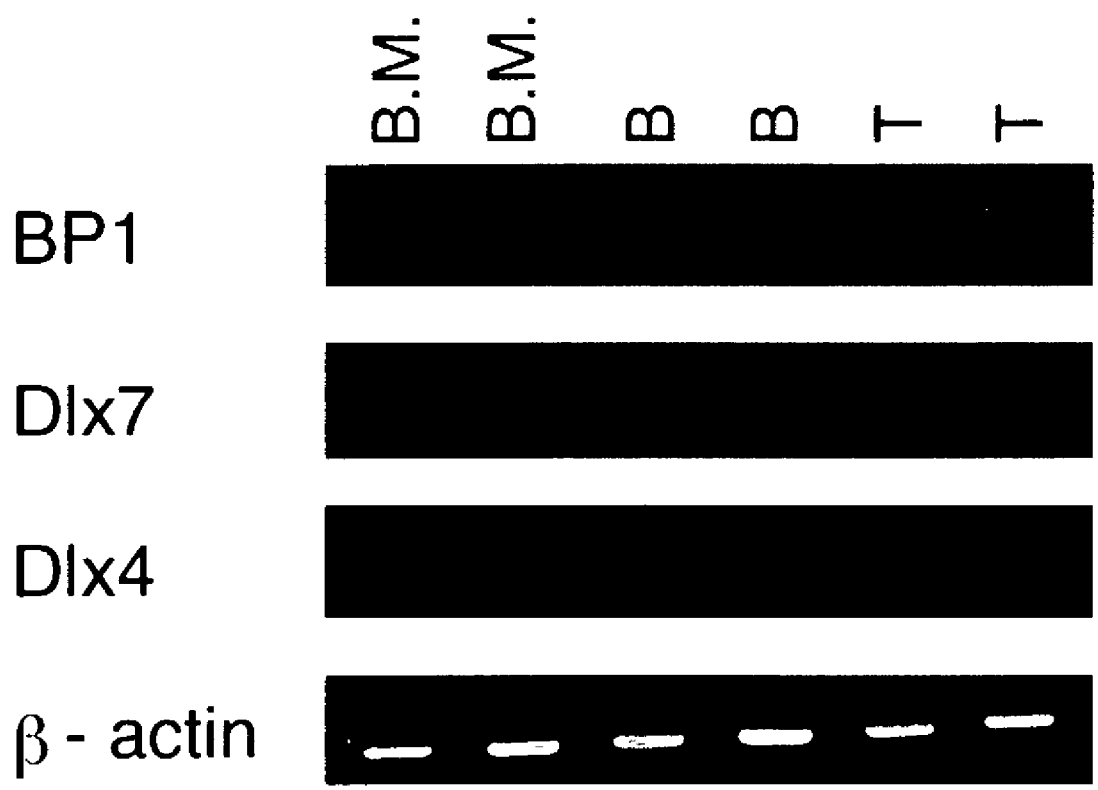

FIG. 9
Patient#  19  27  8  11  34  15  C
− − + + + +
BP1
− − + + + +
Dlx7
− +/− + + + +
Dlx4
β-Actin

SEQUENCE LISTING

<160> NUMBER OF SEQ ID NOS: 25

<210> SEQ ID NO 1
<211> LENGTH: 1251
<212> TYPE: DNA
<213> ORGANISM: Homo sapiens
<220> FEATURE:
<221> NAME/KEY: misc_feature
<222> LOCATION: (633)..(812)

<223> OTHER INFORMATION: homeobox
<220> FEATURE:
<221> NAME/KEY: CDS
<222> LOCATION: (285)..(1004)

<400> SEQUENCE: 1

| | |
|---|---|
| ccgcccgggc aggtgggaac cgaacccgat ggagaggagg gggcccccat ggatttaggg | 60 |
| ggggagggga aagtcatggg ggggcacccc cccggaaccc cttccccagg cgcgcgttct | 120 |
| ccgctgaaag aggctcagag agacactttc tccgggatct taagtgtggg ggctgctggc | 180 |
| tgggggcccc gtccggccca acgccggagg cttggaaaag agagttagca gcgggagcgg | 240 |
| actacgtgcc gggccatggc ccttctgccc gggccctggc caca atg acc tct ttg | 296 |
|                                                                                                                            Met Thr Ser Leu<br>                                                                                                                           1 | |
| ccc tgc ccc ctc ccc ggc cgg gac gcc tcc aaa gct gtc ttc cca gac<br>Pro Cys Pro Leu Pro Gly Arg Asp Ala Ser Lys Ala Val Phe Pro Asp<br>5                     10                    15                  20 | 344 |
| ctc gcc cct gtc ccg tcg gta gcg gct gcc tac ccg ctt ggc ttg tcc<br>Leu Ala Pro Val Pro Ser Val Ala Ala Ala Tyr Pro Leu Gly Leu Ser<br>                        25                    30                    35 | 392 |
| cct aca acc gca gcc tcc ccc aat ttg tcc tac tcc agg ccg tat ggc<br>Pro Thr Thr Ala Ala Ser Pro Asn Leu Ser Tyr Ser Arg Pro Tyr Gly<br>                  40                    45                    50 | 440 |
| cac ctc ctg tct tac ccc tac acc gag cca gcg aac ccc gga gac tcc<br>His Leu Leu Ser Tyr Pro Tyr Thr Glu Pro Ala Asn Pro Gly Asp Ser<br>        55                    60                    65 | 488 |
| tac ctg tcc tgc cag caa ccc gcg gcg ctc tct cag ccc ctc tgc gga<br>Tyr Leu Ser Cys Gln Gln Pro Ala Ala Leu Ser Gln Pro Leu Cys Gly<br>70                    75                    80 | 536 |
| cct gca gag cac cct cag gaa ctc gag gca gac tcg gag aag ccg cgg<br>Pro Ala Glu His Pro Gln Glu Leu Glu Ala Asp Ser Glu Lys Pro Arg<br>85                    90                    95                 100 | 584 |
| ctg tcc ccg gaa ccc tcc gag cgg cgc cct cag gcc ccc gcc aaa aag<br>Leu Ser Pro Glu Pro Ser Glu Arg Arg Pro Gln Ala Pro Ala Lys Lys<br>                        105                 110                 115 | 632 |
| ctc cgc aag ccg agg acc atc tac tcc agc ctg cag ctg cag cac cta<br>Leu Arg Lys Pro Arg Thr Ile Tyr Ser Ser Leu Gln Leu Gln His Leu<br>                 120                 125                 130 | 680 |
| aac cag cgt ttc cag cac acg cag tac ctg gcg ctg ccc gag agg gcc<br>Asn Gln Arg Phe Gln His Thr Gln Tyr Leu Ala Leu Pro Glu Arg Ala<br>                 135                 140                 145 | 728 |
| cag ctg gca gcg cag ctc ggc ctc acc cag acc cag gta aag atc tgg<br>Gln Leu Ala Ala Gln Leu Gly Leu Thr Gln Thr Gln Val Lys Ile Trp<br>150                   155                 160 | 776 |
| ttt cag aac aaa cgc tcc aag tat aag aag ctc ctg aag cag aat tct<br>Phe Gln Asn Lys Arg Ser Lys Tyr Lys Lys Leu Leu Lys Gln Asn Ser<br>165                   170                 175                 180 | 824 |
| ggg ggg cag gaa ggg gac ttc cct ggg agg acc ttc tct gtg tct ccc<br>Gly Gly Gln Glu Gly Asp Phe Pro Gly Arg Thr Phe Ser Val Ser Pro<br>                 185                 190                 195 | 872 |
| tgc tcc cca ccc ctc ccc tcc ctc tgg gat cta ccc aag gca ggg acc<br>Cys Ser Pro Pro Leu Pro Ser Leu Trp Asp Leu Pro Lys Ala Gly Thr<br>                 200                 205                 210 | 920 |
| ctg ccc acc agt ggc tat ggc aac agc ttt gga gcc tgg tat cag cat<br>Leu Pro Thr Ser Gly Tyr Gly Asn Ser Phe Gly Ala Trp Tyr Gln His<br>                 215                 220                 225 | 968 |
| cac tcc tca gat gtc ctg gct tcg cct cag atg atg tgaatctggg<br>His Ser Ser Asp Val Leu Ala Ser Pro Gln Met Met<br>230                   235                 240 | 1014 |

```
gaagggcggg tcaggcccac agccttcctg caaagcccag gacccaggca gtccacctgc    1074
accccttctg ggctgggagg aaaccagctc cagatgggtt ttctctggag gacaaacagt    1134
tagaggagaa aaaggaatgg agcagagcct gtacccctaa ccctaacagc taaatcaagg    1194
acctcagcct tatataatca ttgtccccac cactaccatg gactgaacac cttcacc      1251
```

<210> SEQ ID NO 2
<211> LENGTH: 240
<212> TYPE: PRT
<213> ORGANISM: Homo sapiens
<220> FEATURE:
<221> NAME/KEY: misc_feature
<222> LOCATION: (117)..(177)
<223> OTHER INFORMATION: homeobox

<400> SEQUENCE: 2

```
Met Thr Ser Leu Pro Cys Pro Leu Pro Gly Arg Asp Ala Ser Lys Ala
1               5                   10                  15

Val Phe Pro Asp Leu Ala Pro Val Pro Ser Val Ala Ala Tyr Pro
            20                  25                  30

Leu Gly Leu Ser Pro Thr Thr Ala Ala Ser Pro Asn Leu Ser Tyr Ser
        35                  40                  45

Arg Pro Tyr Gly His Leu Leu Ser Tyr Pro Tyr Thr Glu Pro Ala Asn
    50                  55                  60

Pro Gly Asp Ser Tyr Leu Ser Cys Gln Gln Pro Ala Ala Leu Ser Gln
65                  70                  75                  80

Pro Leu Cys Gly Pro Ala Glu His Pro Gln Glu Leu Glu Ala Asp Ser
                85                  90                  95

Glu Lys Pro Arg Leu Ser Pro Glu Pro Ser Glu Arg Arg Pro Gln Ala
            100                 105                 110

Pro Ala Lys Lys Leu Arg Lys Pro Arg Thr Ile Tyr Ser Ser Leu Gln
        115                 120                 125

Leu Gln His Leu Asn Gln Arg Phe Gln His Thr Gln Tyr Leu Ala Leu
    130                 135                 140

Pro Glu Arg Ala Gln Leu Ala Ala Gln Leu Gly Leu Thr Gln Thr Gln
145                 150                 155                 160

Val Lys Ile Trp Phe Gln Asn Lys Arg Ser Lys Tyr Lys Lys Leu Leu
                165                 170                 175

Lys Gln Asn Ser Gly Gly Gln Glu Gly Asp Phe Pro Gly Arg Thr Phe
            180                 185                 190

Ser Val Ser Pro Cys Ser Pro Leu Pro Ser Leu Trp Asp Leu Pro
        195                 200                 205

Lys Ala Gly Thr Leu Pro Thr Ser Gly Tyr Gly Asn Ser Phe Gly Ala
    210                 215                 220

Trp Tyr Gln His His Ser Ser Asp Val Leu Ala Ser Pro Gln Met Met
225                 230                 235                 240
```

<210> SEQ ID NO 3
<211> LENGTH: 55
<212> TYPE: DNA
<213> ORGANISM: Artificial Sequence
<220> FEATURE:
<221> NAME/KEY: misc_feature
<222> LOCATION: (1)..(55)
<223> OTHER INFORMATION: synthesized oligonucleotide

<400> SEQUENCE: 3

```
tgtatatata cacatatata tatatatttt ttttcctttt cttaccagaa ggttt         55
```

<210> SEQ ID NO 4
<211> LENGTH: 56
<212> TYPE: DNA
<213> ORGANISM: Artificial Sequence
<220> FEATURE:
<221> NAME/KEY: misc_feature
<222> LOCATION: (1)..(56)
<223> OTHER INFORMATION: synthesized oligonucleotide

<400> SEQUENCE: 4
tgtacatata cacatatata tatatatata tttttctttt tcttaccaga aggttt         56

<210> SEQ ID NO 5
<211> LENGTH: 58
<212> TYPE: DNA
<213> ORGANISM: Artificial Sequence
<220> FEATURE:
<221> NAME/KEY: misc_feature
<222> LOCATION: (1)..(58)
<223> OTHER INFORMATION: synthesized oligonucleotide

<400> SEQUENCE: 5
ttcttatttg tgtaataaga aaattgggaa aacgatcttc aatatgctta ccaagctg       58

<210> SEQ ID NO 6
<211> LENGTH: 48
<212> TYPE: DNA
<213> ORGANISM: Artificial Sequence
<220> FEATURE:
<221> NAME/KEY: misc_feature
<222> LOCATION: (1)..(48)
<223> OTHER INFORMATION: synthesized oligonucleotide

<400> SEQUENCE: 6
ttcttttaat ggatatttat ttcaatataa taaaaaatta gagtttta                  48

<210> SEQ ID NO 7
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthesized oligonucleotide

<400> SEQUENCE: 7
tgcatatata tgtatatgta tgtgtgtata                                      30

<210> SEQ ID NO 8
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: synthesized oligonucleotide

<400> SEQUENCE: 8
cacctcctgt cttaccccta cacc                                            24

<210> SEQ ID NO 9
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: synthesized oligonucleotide

```
<400> SEQUENCE: 9
gcccttcccc agattcacat catc                                           24

<210> SEQ ID NO 10
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: synthesized oligonucleotide

<400> SEQUENCE: 10
gtatggccac ctcctgtctt                                                20

<210> SEQ ID NO 11
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: synthesized oligonucleotide

<400> SEQUENCE: 11
gagtagatgg tcctcggctt                                                20

<210> SEQ ID NO 12
<211> LENGTH: 240
<212> TYPE: PRT
<213> ORGANISM: Homo sapiens
<220> FEATURE:
<221> NAME/KEY: HELIX 1
<222> LOCATION: (127)..(136)
<220> FEATURE:
<221> NAME/KEY: HELIX 2
<222> LOCATION: (144)..(154)
<220> FEATURE:
<221> NAME/KEY: HELIX 3
<222> LOCATION: (158)..(173)

<400> SEQUENCE: 12
```

Met Thr Ser Leu Pro Cys Pro Leu Pro Gly Arg Asp Ala Ser Lys Ala
1               5                   10                  15

Val Phe Pro Asp Leu Ala Pro Val Pro Ser Val Ala Ala Tyr Pro
                20                  25                  30

Leu Gly Leu Ser Pro Thr Thr Ala Ala Ser Pro Asn Leu Ser Tyr Ser
            35                  40                  45

Arg Pro Tyr Gly His Leu Leu Ser Tyr Pro Tyr Thr Glu Pro Ala Asn
    50                  55                  60

Pro Gly Asp Ser Tyr Leu Ser Cys Gln Gln Pro Ala Ala Leu Ser Gln
65                  70                  75                  80

Pro Leu Cys Gly Pro Ala Glu His Pro Gln Glu Leu Glu Ala Asp Ser
                85                  90                  95

Glu Lys Pro Arg Leu Ser Pro Glu Pro Ser Glu Arg Arg Pro Gln Ala
            100                 105                 110

Pro Ala Lys Lys Leu Arg Lys Pro Arg Thr Ile Tyr Ser Ser Leu Gln
        115                 120                 125

Leu Gln His Leu Asn Gln Arg Phe Gln His Thr Gln Tyr Leu Ala Leu
    130                 135                 140

Pro Glu Arg Ala Gln Leu Ala Ala Gln Leu Gly Leu Thr Gln Thr Gln
145                 150                 155                 160

```
Val Lys Ile Trp Phe Gln Asn Lys Arg Ser Lys Tyr Lys Lys Leu Leu
            165                 170                 175

Lys Gln Asn Ser Gly Gly Gln Glu Gly Asp Phe Pro Gly Arg Thr Phe
        180                 185                 190

Ser Val Ser Pro Cys Ser Pro Pro Leu Pro Ser Leu Trp Asp Leu Pro
        195                 200                 205

Lys Ala Gly Thr Leu Pro Thr Ser Gly Tyr Gly Asn Ser Phe Gly Ala
        210                 215                 220

Trp Tyr Gln His His Ser Ser Asp Val Leu Ala Ser Pro Gln Met Met
225                 230                 235                 240

<210> SEQ ID NO 13
<211> LENGTH: 19
<212> TYPE: PRT
<213> ORGANISM: Artificial Sequence
<220> FEATURE:
<221> NAME/KEY: misc_feature
<222> LOCATION: (1)..(19)
<223> OTHER INFORMATION: synthesized polypeptide antigen

<400> SEQUENCE: 13

Ser Tyr Pro Tyr Thr Glu Pro Ala Asn Pro Gly Asp Ser Tyr Leu Ser
1               5                   10                  15

Cys Gln Gln

<210> SEQ ID NO 14
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: synthesized oligonucleotide

<400> SEQUENCE: 14
cctacaccgt gttgtgctgc                                              20

<210> SEQ ID NO 15
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: synthesized oligonucleotide

<400> SEQUENCE: 15
ctgttgccat agccactg                                                18

<210> SEQ ID NO 16
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: synthesized oligonucleotide

<400> SEQUENCE: 16
cacggtgtgg cgggggagac at                                           22

<210> SEQ ID NO 17
<211> LENGTH: 22
<212> TYPE: DNA
```

```
<213> ORGANISM: Artificial Sequence
<220> FEATURE:
<221> NAME/KEY: misc_feature
<222> LOCATION: (1)..(22)
<223> OTHER INFORMATION: synthesized oligonucleotide

<400> SEQUENCE: 17
ctgcggtggg aggtcggagt tc                                              22

<210> SEQ ID NO 18
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: synthesized oligonucleotide
<300> PUBLICATION INFORMATION:
<301> AUTHORS: Raff T, van der Giet M, Endemann D, Wiederholt T, Paul M.
<302> TITLE: Design and testing of  beta-actin  primers for RT-PCR that
      do not co-amplify processed pseudogenes.
<303> JOURNAL: Biotechniques
<304> VOLUME: 23
<305> ISSUE: 3
<306> PAGES: 456-460
<307> DATE: 1997
<313> RELEVANT RESIDUES: (1)..(23)

<400> SEQUENCE: 18
ggatcttcat gaggtagtca gtc                                             23

<210> SEQ ID NO 19
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: synthesized oligonucleotide
<300> PUBLICATION INFORMATION:
<301> AUTHORS: Raff T, van der Giet M, Endemann D, Wiederholt T, Paul M.
<302> TITLE: Design and testing of  beta-actin  primers for RT-PCR that
      do not co-amplify processed pseudogenes.
<303> JOURNAL: Biotechniques
<304> VOLUME: 23
<305> ISSUE: 3
<306> PAGES: 456-460
<307> DATE: 1997
<313> RELEVANT RESIDUES: (1)..(18)

<400> SEQUENCE: 19
cctcgccttt gccgatcc                                                   18

<210> SEQ ID NO 20
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: synthesized oligonucleotide
<300> PUBLICATION INFORMATION:
<301> AUTHORS: Majello B, Kenyon LC, Dalla-Favera R.
<302> TITLE: Human c-myb protooncogene: nucleotide  sequence of  cDNA
      and organization of the genomic locus.
<303> JOURNAL: Proc Natl Acad Sci
<304> VOLUME: 23
<305> ISSUE: 24
<306> PAGES: 9636-9640
<307> DATE: 1986
<313> RELEVANT RESIDUES: (1)..(23)

<400> SEQUENCE: 20
```

```
attaggtaat gaattgtagc cag                                          23
```

<210> SEQ ID NO 21
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: synthesized oligonucleotide
<300> PUBLICATION INFORMATION:
<301> AUTHORS: Shimamoto T, Nakamura S, Bollekens J, Ruddle FH and
       Takeshita K
<302> TITLE: Inhibition of Dlx-7 homeobox gene causes decreased
       expression of GATA-1 and c-myc genes and apoptosis
<303> JOURNAL: Proc. Natl. Acad. Sci. USA
<304> VOLUME: 94
<305> ISSUE: 7
<306> PAGES: 9636-9640
<307> DATE: 1997
<313> RELEVANT RESIDUES: (1)..(23)

<400> SEQUENCE: 21

```
acttagagta atgcttttac tga                                          23
```

<210> SEQ ID NO 22
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: synthesized oligonucleotide
<300> PUBLICATION INFORMATION:
<301> AUTHORS: Tsai SF, Martin DIK, Zon LI, D'Andrea AD, Wong GG, Orkin
       SH.
<302> TITLE: Cloning of the cDNA for the major DNA-binding protein of
       the erythroid lineage through expression in mammalian cells.
<303> JOURNAL: Nature
<304> VOLUME: 339
<305> ISSUE: 6224
<306> PAGES: 446-451
<307> DATE: 1989
<313> RELEVANT RESIDUES: (1)..(23)

<400> SEQUENCE: 22

```
ccattgctca actgtatgga ggg                                          23
```

<210> SEQ ID NO 23
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: synthesized oligonucleotide
<300> PUBLICATION INFORMATION:
<301> AUTHORS: Shimamoto T, Nakamura S, Bollekens J, Ruddle FH and
       Takeshita K
<302> TITLE: Inhibition of Dlx-7 homeobox gene causes decreased
       expression of GATA-1 and c-myc genes and apoptosis.
<303> JOURNAL: Proc. Natl. Acad. Sci. USA
<304> VOLUME: 94
<305> ISSUE: 7
<306> PAGES: 3245-3249
<307> DATE: 1997
<313> RELEVANT RESIDUES: (1)..(23)

<400> SEQUENCE: 23

```
actattgggg acagggagtg atg                                          23
```

```
<210> SEQ ID NO 24
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: synthesized oligonucleotide
<300> PUBLICATION INFORMATION:
<301> AUTHORS: Chen Q, Cheng J-T, Tsai L-H, Schneider N, Buchanan G,
       Carroll A, Crist W, Ozanne B,  Siciliano MJ, Baer R.
<302> TITLE: The tal gene undergoes chromosome translocation in T cell
       leukemia and potentially encodes a helix-loop-helix protein.
<303> JOURNAL: EMBO J
<304> VOLUME: 9
<305> ISSUE: 2
<306> PAGES: 415-424
<307> DATE: 1990
<313> RELEVANT RESIDUES: (1)..(24)

<400> SEQUENCE: 24
caatcgagtg aagaggagac ctcc                                          24

<210> SEQ ID NO 25
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: synthesized oligonucleotide
<300> PUBLICATION INFORMATION:
<301> AUTHORS: Chen Q, Cheng J-T, Tsai L-H, Schneider N, Buchanan G,
       Carroll A, Crist W, Ozanne B,  Siciliano MJ, Baer R.
<302> TITLE: The tal gene undergoes chromosome translocation in T cell
       leukemia and potentially encodes a helix-loop-helix protein.
<303> JOURNAL: EMBO J
<304> VOLUME: 9
<305> ISSUE: 2
<306> PAGES: 415-424
<307> DATE: 1990
<313> RELEVANT RESIDUES: (1)..(20)

<400> SEQUENCE: 25
ttgcggagct cggcaaaggc                                               20
```

US 7,176,294 B2

TRANSCRIPTION FACTOR, BP1

This application is a divisional of application Ser. No. 09/636,735, filed Aug. 11, 2000, now issued as U.S. Pat. No. 6,416,956.

The present application claims the benefit of the filing date of U.S. Provisional Application No. 60/148,940, filed Aug. 13, 1999. The provisional application is incorporated by reference herein.

STATEMENT AS TO FEDERALLY SPONSORED RESEARCH

Work described herein was supported by NIH grant R01DK53533. The U.S. Government has certain rights in the invention.

BACKGROUND OF THE INVENTION

1. Field of the Invention

The present invention relates to a DNA that encodes the transcription factor BP1, a vector containing the DNA and a host cell containing the DNA. The invention also relates to an antisense DNA or RNA to the DNA encoding BP1, methods for treating sickle cell anemia by administering an effective amount of BP1, and methods for screening for acute myeloid leukemia, acute lymphocytic leukemia, and breast cancer.

(In the provisional application, the transcription factor BP1 was sometimes called "BP1/Dlx9" or "BP1/Dlx9". Herein, for greater clarity, the transcription factor is simply referred to as "BP1".)

2. Description of the Related Art

Expression of globin genes in the β-globin cluster is restricted to erythropoietic cells, with five different genes expressed during embryonic (ε), fetal (Gγ and Aγ) and adult (δ and β) development. Transcriptional activation of globin genes occurs not only by binding of transcriptional activator proteins to the promoter of the gene being activated, but also by a regulatory element located 6–18 kb upstream of the β-globin cluster, the Locus Control Region (LCR) (See, for example, Berg, P. E. and A. N. Schechter. 1992. Molecular genetics of disorders of hemoglobin. In T. Friedmann (ed), Molecular Genetic Medicine, Academic Press, San Diego, Forrester, W. C., C. Thompson, J. T. Elder, and Groudine, M. 1986. A developmentally stable chromatin structure in the human β-globin gene cluster. Proc. Natl. Acad. Sci., USA 83: 1359–1363; and Tuan, D., W. Soloman, Q. Li, and I. M. London, 1985. The "β-like-globin" gene domain in human erythroid cells. Proc. Natl. Acad. Sci. USA 82: 6384–6388.). Sequential activation of the β-globin cluster genes during ontogeny must be countered by repression of the globin genes inactive during a given developmental stage. Repression is caused by binding of repressor proteins to promoter/upstream DNA and, in the case of the adult β-globin gene, is probably also due to lack of activation by the LCR (see, for example, Crossley, M. and S. H. Orkin. 1993. Regulation of the β-globin locus. Curr. Opinion Gen. Dev. 3: 232–237.). While much is known about transcriptional activators that bind to DNA sequences near the β-globin gene, little is known about the proteins that repress its transcription.

As discussed below, BP1 is shown to bind to two silencer DNA sequences upstream of the β-globin gene and therefore, there is strong evidence suggesting that BP1 protein is a repressor of the β-globin gene. The present invention provides for a DNA sequence that encodes BP1, and methods of using information derived from knowledge of the DNA sequence to screen for conditions such as breast cancer, acute myeloid leukemia and acute lymphocytic leukemia. The DNA sequence was found to be closely related to two other human genes, DLX4 and DLX7, described in Quinn, L. M., B. V. Johnson, J. Nicholl, G. R. Sutherland, and B. Kalionis. 1997. Isolation and identification of homeobox genes from human placenta including a novel member of the Distal-less family, DLX4. Gene 187: 55–61 and Nakamura S, Stock D W, Wydner K L, Bollekens J A, Takeshita K, Nagai B M, Chiba, Kitamura T, Freeland T M, Zhao Z, Minowada J, Lawrence J B, Weiss K B, and Ruddle F H. Genomic analysis of a new mammalian Distal-less gene: Dlx-7. *Genomics* 1996; 38: 314–324.

Survival rates for many types of cancers correlate with early detection and treatment. Further, it is helpful to monitor ongoing cancer treatments to determine effectiveness. Accordingly, there is a continuing need for reliable cancer cell screening methods. One method of screening is to detect and monitor the expression of genes that are overexpressed or underexpressed in particular types of cancer cells, in comparison to normal cells. Detection techniques and particular markers have been disclosed, for example, in the following U.S. patents, incorporated herein by reference: U.S. Pat. No. 5,776,683 to Smith et al; U.S. Pat. No. 5,965,409 to Pardee et al; U.S. Pat. No. 6,037,129 to Cole, et al; U.S. Pat. No. 5,677,125 to Holt, et al; U.S. Pat. No. 6,004,756 to Watson, et al; U.S. Pat. No. 5,994,062 to Mulshine, et al; U.S. Pat. No. 5,700,927 to Zon, et al; and U.S. Pat. No. 5,981,218 to Rio et al.

Because no marker or method of screening is completely reliable, there is a continuing need in the art for additional genetic markers. In particular, there is a continuing need for genetic markers for identifying breast cancer, acute myeloid leukemia and acute lymphocytic leukemia. The present invention overcomes this problem in the art by providing DNA BP1 compositions and methods for screening for breast cancer, acute myeloid leukemia and acute lymphocytic leukemia.

The problem also exists in the art of lack of information regarding repression of the β-globin gene. As discussed below, there are medical conditions such as sickle cell anemia that can be treated by repressing the expression of β-globin and the present invention, provides for the production of BP1, a putative β-globin repressor.

SUMMARY OF THE INVENTION

It is an object of the present invention to provide a DNA sequence encoding BP1.

It is a further object of the present invention to provide a marker and a method for detecting acute myeloid leukemia and acute lymphocytic leukemia.

It is a further object of the present invention to provide a marker and a method for detecting breast cancer.

It is a further object of the present invention to provide a treatment for conditions that can be alleviated by repressing the expression of the β-globin gene.

It is a further object of the present invention to provide a treatment for sickle cell anemia.

It is a further object of the present invention to provide a treatment for conditions that can be alleviated by blocking the expression of BP1.

These and other objects are achieved in present invention by providing an isolated DNA having SEQ ID NO:1, encoding BP1. BP1 exhibits a repressor function: it binds to Silencers I and II upstream of the β-globin gene and binds to a sequence of −530 bp upstream of the δ-globin gene.

The invention also includes a vector comprising the DNA encoding BP1 and a host cell transformed with the vector.

In an alternative embodiment, the invention is directed to an antisense DNA or an antisense RNA of a DNA having SEQ ID NO:1, encoding BP1.

The invention further provides a method of treating sickle cell anemia comprising administering an effective amount of BP1.

The invention provides a method of screening for and/or diagnosing acute myeloid leukemia or acute lymphocytic leukemia, the method comprising the steps of (a) obtaining a cell sample from a patient, and (b) determining whether BP1 is overexpressed by said cell sample as compared to normal cells.

The invention also provides a method of screening for and/or diagnosing breast cancer, the method comprising the steps of (a) obtaining a cell sample from a patient, and (b) determining whether BP1 is overexpressed by said cell sample as compared to normal cells.

The invention further provides for a polyclonal antibody to BP1.

The invention further provides a set of PCR primers for amplifying the DNA of SEQ ID NO. 1.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF THE DRAWINGS

FIG. 4 is the sequence of BP1. This sequence is also set forth in the attached sequence listing as SEQ ID NO:1. The open reading frame of the sequence is indicated as well as the predicted protein sequence, which is also set forth in the sequence listing as SEQ ID NO:2 and SEQ ID NO: 12.

In FIG. 5A, pϵCAT/SI was the target DNA; in FIG. 5B, pϵCAT/SII was the target DNA. K562 cells were transiently co-transfected with increasing amounts of either an empty vector or pRSV/BP1-ORF, along with a target plasmid.

FIG. 8 is an autoradiogram showing the expression of BP1, DLX7 and DLX4 in normal bone marrow, B-cells and T cells. Semi-quantitative RT-PCR was used to measure expression.

FIG. 9 is an autoradiogram showing the expression of BP1, DLX7 and DLX4 in acute myeloid leukemia. Samples from six patients are shown. (−) indicates expression equal to or less than normal controls; (+) indicates expression greater than controls; (+)indicates an expression ratio at least three times greater than the ratio for (+).

DETAILED DESCRIPTION OF THE PREFERRED EMBODIMENTS

Figure 1:
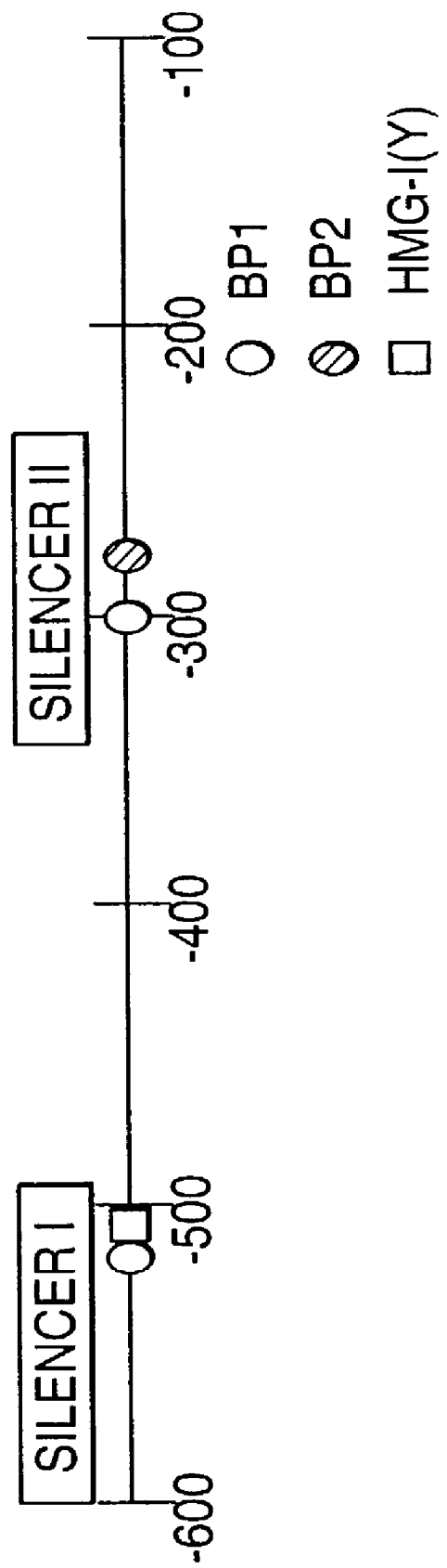
FIG. 1 is a schematic representation of the region −100 to −600 bp upstream of the β-globin, showing that BP1 binds within Silencer I at −530 bp relative to the cap site (+1) and within Silencer II at −300 bp, and that BP2, another DNA-binding protein, binds within Silencer II at −270 bp.

The present invention relates to an isolated DNA, having or consisting essentially of SEQ ID NO:1 and encoding the transcription factor BP1. The transcription factor BP1 exhibits β-globin repressor function and binds to Silencers I and II upstream of the β-globin gene, to a sequence of −530 bp upstream of the δ-globin gene and to an Indian haplotype D sequence. BP1 is typically expressed in placenta and kidney. The predicted sequence of BP1, deduced from the open reading frame of the isolated DNA of SEQ ID NO:1, is given as SEQ ID NOs: 2 and 12. Both the DNA sequence and the protein sequence are shown together in FIG. 4. As used herein, the term "isolated DNA" refers to DNA that is not in its native environment.

In a preferred embodiment of the invention, the isolated DNA encoding BP1 is a cDNA of 1251 bp. The isolated DNA also comprises an open reading frame (ORF).

The present invention further relates to a vector containing the DNA and to a host cell transformed with the vector containing the DNA. In a preferred embodiment, the transformed host cell is a eukaryotic host cell.

The invention further includes an antisense DNA or an antisense RNA of a DNA having SEQ ID NO:1.

The invention further includes a method of treating sickle cell anemia, the method comprising the step of administering an effective amount of BP1 to a patient in need thereof. In the method of the invention, BP1 decreases β-globin expression in the patient and decreases intracellular concentrations of HbS.

The invention further includes a method of screening for and diagnosing acute myeloid leukemia or acute lymphocytic leukemia, the method comprising the steps of
(a) obtaining a cell sample from a patient, and
(b) determining if BP1 is overexpressed by said cell sample as compared to normal cells.

The invention also includes a method of screening for and diagnosing breast cancer, the method comprising the steps of
(a) obtaining a cell sample from a patient, and
(b) determining if BP1 is overexpressed by said cell sample as compared to normal cells.

In the methods for detecting leukemia and breast cancer, the overpression of BP1 may determined by detecting BP1-encoding mRNA by reverse transcriptase polymerase chain reaction (RT-PCR) or by detecting BP1 itself by immunohistochemical detection.

The invention further includes PCR primers that amplify a unique DNA molecule from a substrate of cDNA of mRNA that encodes for BP1. Such PCR primers can be readily derived from the DNA sequence of SEQ ID NO.: 1. As used herein, the term "unique DNA molecules" means that the DNA is of sufficient specificity to determine that the substrate being amplified originated from the sequence of SEQ ID NO:1.

The invention further includes polyclonal and monoclonal antibodies to BP1. A polyclonal antibody can be obtained by immunizing a mammal with BP1 or an antigenic fragment thereof in order to induce the production of sera containing polyclonal antibodies, as described below. A monoclonal antibody to BP1 may be obtained by hybridoma technology, which typically includes the further steps of isolating splenocytes from immunized mammals, fusing them with myeloma cells, then identifying fused cells that secrete antibodies that bind to BP1.

The invention further includes a method of repressing the β-globin gene comprising administering an effective amount of BP1.

These aspects of the invention are further characterized below. First, it is shown that the cloning of BP1 cDNA and that its overexpression in a transient co-transfection assay causes repression of a reporter gene linked to either Silencer I or Silencer II DNA of the β-globin gene. This provides evidence that BP1 is a repressor of the β-globin gene. Sequencing reveals that the DNA encoding BP1 contains a homeobox, placing the DNA in a family of conserved genes that regulate each other and that regulate unrelated genes as well (see, for example, Jaynes, J. B. P. H. and O'Farrell, 1988 Activation and repression of transcription by homeodomain-containing proteins that bind a common site. Nature 336: 744–749 and references therein; Levine, M. and T. Hoey, 1988. Homeobox proteins as sequence-specific transcription factors, Cell 55: 537–540.). Sequence comparison indicates that the DNA encoding BP1 belongs to the Distal-less family of homeobox genes, which are expressed during early development (see, for example, Cohen, S. M. and G. Jurgens. 1989. Proximal-distal pattern formation in *Drosophila*: cell autonomous requirement for Distal-less gene activity in limb development. EMBO J 8: 2045–2055; Cohen, S. M., G. Bronner, F. Kuttner, G. Jurgens, and H. Jackle, 1989. Distal-less encodes a homeodomain protein required for limb development in *Drosophila*. Nature 338: 432–434; Dolle, P., M. Price and D. Duboule. 1992. Expression of the murine Dlx-1 homeobox gene during facial, ocular, and limb development. Differentiation 49: 93–99; Robinson, G. W. and K. Mahon. 1994. Differential and overlapping expression domains of Dlx-2 and Dlx-3 suggest distinct roles for Distal-less homeobox genes incraniofacial development. Mech. Dev. 48: 199–215; Simeone, A., D. Acampora, M. Pannese, M. D'Esposito, A. Stornaiuolo, M. Gulisano, A. Mallamaci, K. Kastury, T. Druck, and K. Huebner. 1994. Cloning and characterization of two members of the vertebrate Dlx gene family. Proc. Natl. Acad. Sci. USA 91: 2250–54; and Stock, D. W., D. L. Ellies, Z. Zhao, M. Ekker, F. H. Ruddle, and K. M. Weiss. 1996. The evolution of the vertebrate Dlx family. Proc. Natl. Acad. Sci. USA 93: 10858–10863.). The expression of the DNA encoding BP1 is highly restricted, which is a characteristic of developmentally important genes.

Cloning and Characterizing BP1

Materials and Methods:

Cloning BP1: A λgt11 K562 cell cDNA expression library (Clontech, Inc.) was screened with an oligonucleotide probe containing the BP1 binding site located in Silencer II DNA, which included sequences between −336 and −278 bp upstream of the β-globin gene. Screening was as described (see, for example, Vinson, C. R., K. L. LaMarco, P. F. Johnson, W. H. Landschulz, and S. L. McKnight. 1988. In situ detection of sequence-specific DNA binding activity specified by a recombinant bacteriophage. Genes & Devel. 2: 801–806), with several modifications. Filters were prehybridized in binding buffer (see, for example, Berg, P. E., D. M. Williams, R.-L. Qian, R. B. Cohen, S. X. Cao, M. Mittelman, and A. N. Schechter. 1989. A common protein binds to two silencers 5' to the human β-globin gene. Nucl. Acids Res. 17: 8833–8852) containing 5% Carnation instant dry milk at 4° C. for 30 minutes, then hybridized in the same buffer for 2 to 12 hours at 4° C. with shaking. Positive plaques were purified and subjected to three additional rounds of screening.

Electrophoretic mobility shift assay (EMSA): The binding reaction included 500 pg of fusion protein or 250 ng of nuclear extract added to binding buffer (10 mM Tris, pH 7.5, 50 mM NaCl, 5% glycerol, 1 mM DTT, 1 μl of 1 mg/ml BSA, 1 μg poly(dI-dC)) and 5,000–10,000 cpm of $^{32}$P-dCTP labeled probe. Incubation was for 30 minutes at room temperature. Nuclear extracts were prepared according to Dignam et al (Dignam, J. D., R. M. Lebovitz, and R. G. Roeder. 1983. Accurate transcription initiation by RNA polymerase II in a soluble extract from isolated mammalian nuclei. Nucl. Acids Res. 11: 1475–1489). Protein extracts from lysogens were prepared as described (see, for example, Cowell, I. G. and H. C. Hurst. 199. Cloning transcription factors from a cDNA expression library, p. 120–122. In D. S. Latchman (ed.), Transcription factors: a practical approach. IRL Press, New York). Competitors were pre-incubated with nuclear extract for 20 minutes prior to addition of the probe. Oligonucleotides sequences of probes and competitors for EMSA analyses are shown below.

| Name | Sequence |
|---|---|
| −530 Reference | TGTATATATACACATATATATATATATTTTTTT CTTTTCTTACCAGAAGGTTT (SEQ ID NO:3) |

-continued

| Name | Sequence |
|---|---|
| -530 Indian | TGTACATATACACATATATATATATATATA TTTTTTCTTTTCTTACCAGAAGGTTT (SEQ ID NO:4) |
| -300 beta | TTCTTATTTGTGTAATAAGAAAATTGGGAAAACG ATCTTCAATATGCTTACCAAGCTG (SEQ ID NO:5) |
| -530 delta | TTCTTTTAA TGGATATTTATTTCAATATAAT AAAAAATTAGAGTTTTA (SEQ ID NO:6) |
| non-specific | TGCATATATATGTATATGTATGTGTATA (SEQ ID NO:7) |

Plasmid construction: To construct a plasmid expressing the BP1 cDNA open reading frame, BP1 cDNA was amplified by RT-PCR from K562 cell mRNA. The resulting 1000 bp product was cloned into pGEM7 vector (Promega, Inc.) and its identity confirmed by sequencing. This plasmid was cleaved with Hind III and Xba I to release the BP1 ORF, which was directionally cloned into pRc/RSV (Invitrogen, Inc.).

Transfections and CAT assays: Transient transfection assays were performed in K562 cells using DMRIE-C reagent (Gibco-BRL, Inc.). Cells were grown to a density of $5 \times 10^5$ cells/ml and a total of $2 \times 10^6$ cells were used per transfection reaction. Transfections were performed in six well plates using OPTI-MEM serum-free medium (Gibco-BRL, Inc.). A total of 8 µg of plasmid DNA and salmon sperm DNA were added to complex with 16 ul of DMRIE-C reagent in 1 ml of OPTI-MEM I Reduced Serum Medium (Gibco-BRL, Inc.) for 15–45 min. at room temperature. $2 \times 10^6$ cells in 0.2 ml serum-free medium were added to each well and plates were incubated for 4–5 hrs at 37° C. Two ml of growth medium were added and cells were harvested after 48 hr. CAT assays were performed as described (see, for example, Berg, P. E., D. M. Williams, R.-L. Qian, R. B. Cohen, S. X. Cao, M. Mittelman, and A. N. Schechter. 1989. A common protein binds to two silencers 5' to the human β-globin gene. Nucl. Acids Res. 17: 8833–8852).

Northern blot analysis: RNA was isolated using RNeasy and Oligotex kits (Qiagen, Inc.). Two micrograms of mRNA was electrophoresed per lane, and then transferred to Hybond N membrane (Amersham) by capillary action. RNA was crosslinked to the membrane using a Stratolinker (Stratagene), and the filter was hybridized using either standard methods or a sandwich method, which eliminates the background (see, for example, Wu, S., Q. Lu, and A. L. Kriz. 1995. Multiple-sandwich, one-step hybridization of Northern and Southern blots. BioTechniques 18: 585–586.). An RNA dot blot was purchased (Clontech, Inc.); the amounts of RNA loaded on the blot had been normalized by the manufacturer to eight different housekeeping genes, obviating the need to normalize the samples. The probe was a 630 bp DNA fragment obtained by PCR amplification of BP1 cDNA cloned in pBluescript with subsequent Eco RI digestion to release a partial 3' BP1 cDNA lacking homeobox sequences. It was labeled by random priming and hybridized overnight at 65° C. Blots were washed and exposed to X-ray film.

RT-PCR: Total RNA was isolated using TRIzol Reagent (GIBCO BRL) according to the manufacturer's specifications. One microgram of RNA was reverse transcribed using SuperScript II RT (GIBCO BRL) in a total reaction volume of 20 µl. PCR was performed with 1 µl of reverse-transcription product in 25 µl total reaction volume consisting of 16.8 µl of distilled $H_2O$, 2.5 µl of 10×PCR buffer (200 mM Tris-HCl [pH 8.4], 500 mM KCl), 1.5 µl 25 mM $MgCl_2$, 0.5 µl 10 mM dNTP mix (10 mM each dATP, dCTP, dGTP, dTTP), 0.2 µl (1 unit) Ampli-Taq DNA polymerase (Perkin Elmer) and 1 µl each of 10 µM β-actin or BP1 forward and reverse primers, respectively. Based on linearity assay results, the following PCR conditions for BP1 were used. Each PCR cycle consisted of a denaturation step (94° C., 1 min), an annealing step (58°, 1 minute) and an elongation step (72° C., 1.5 minute) for 27 cycles, followed by an additional extension (72° C., 5 minutes). Primers, designed to amplify a product of 581 bp, were: forward: 5'-CACCTC-CTGTCTTACCCCTACACC-3' SEQ ID NO:8; reverse: 5'-GCCCTTCCCCAGATTCACATCATC-3' SEQ ID NO:9. PCR products were electrophoresed on a 2% agarose gel and visualized with ethidium bromide. The product was verified by cleavage with restriction enzymes and hybridization with an internal probe.

Alternatively, a product of 225 bp may be obtained with the following primers: forward 5'-GTATGGCCACCTCCT-GTCTT-3' (SEQ ID NO: 10) and reverse: 5'-GAGTAGATG-GTCCTCGGCTT-3' (SEQ ID NO: 11) under the following conditions: 94° C. for 2 minutes; then 94° C. for 1 minute, 62° C. for 1 minute and 72° C. for 1.5 minutes, 30 cycles; 72° C. for 10 minutes.

Cloning of BP1 cDNA:

A λgt11 cDNA expression library made from human K562 cells was probed using a multimerized oligonucleotide containing the −300 bp BP1 binding site. Two million plaques were screened and one positive plaque was isolated that expressed a protein that recognized the −300 bp BP1 binding site but not a negative control sequence.

Figure 2:
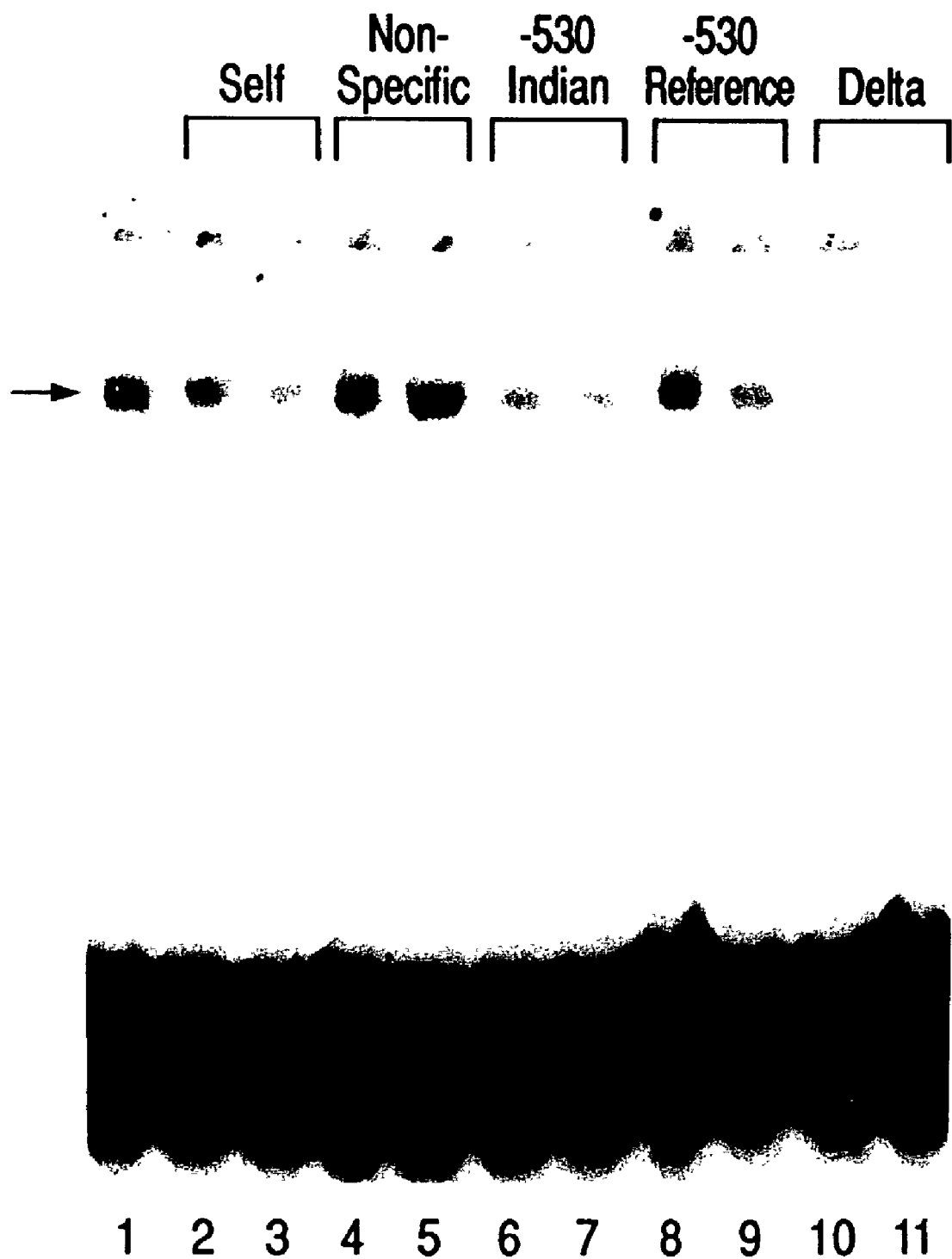
FIG. 2 is an autoradiogram showing the results of an EMSA competition assay to verify that the cDNA encoded a protein with the expected binding specificities of BP1, namely, the ability to bind to Silencers I and II upstream of the β-globin gene and to a sequence −530 bp upstream of the δ-globin gene. The putative BP1 protein, fused to β-galactosidase, was expressed from a λ lysogen. This fusion protein was partially purified and incubated with the Silencer II probe used for screening the library, resulting in a single shifted band, indicated by the arrow, lane 1.

To verify that the cDNA encoded a protein with the expected binding specificities of BP1, namely, the ability to bind to Silencers I and II upstream of the β-globin gene and to a sequence −530 bp upstream of the δ-globin gene (see, for example, Berg, P. E., S. Abhyankar, and M. Chase. 1994. The high mobility group protein HMG-I(Y) binds to a silencer DNA sequence upstream of the human β-globin gene. Blood 84 Suppl 1:262a), an EMSA competition assay was performed. The putative BP1 protein, fused to β-galactosidase, was expressed from a λ lysogen, as described above. This fusion protein was partially purified and incubated with the Silencer II probe used for screening the library, resulting in a single shifted band, indicated by the arrow (FIG. 2, lane 1). The band at the top marks the position of the wells, and the band at the bottom contains the unshifted probe. Cold competitors were added at a 100× and 200× molar excess to determine specificity. The shifted band was competed by self DNA (unlabeled −300 binding site, lanes 2–3), the BP1 binding site at −530 bp in Silencer I containing either the reference (wild type) or Indian haplotype sequences (lanes 6–9), and the BP1 binding site found upstream of the δ-globin gene (lanes 10–11), but not to a non-specific DNA (lanes 4–5). Note that the Indian sequence is a better competitor than the reference sequence, indicating tighter binding of BP1 to the Indian sequence, as was previously observed using K562 nuclear extracts (see, for example, Elion, J., P. E. Berg, C. Lapoumeroulie, G. Trabuchet, M. Mittelman, R. Krishnamoorthy, A. N. Schechter, and D. Labie. 1992. DNA sequence variation in a negative control region 5' to the β-globin gene correlates with the phenotypic expression of the $\beta^5$ mutation. Blood 79: 787–792.). A negative control, pure β-galactosidase protein, did not exhibit binding activity towards the probe (data not shown). The EMSA analysis thus demonstrated that the binding properties of the fusion protein conform to those expected for BP1.

Figure 3B:
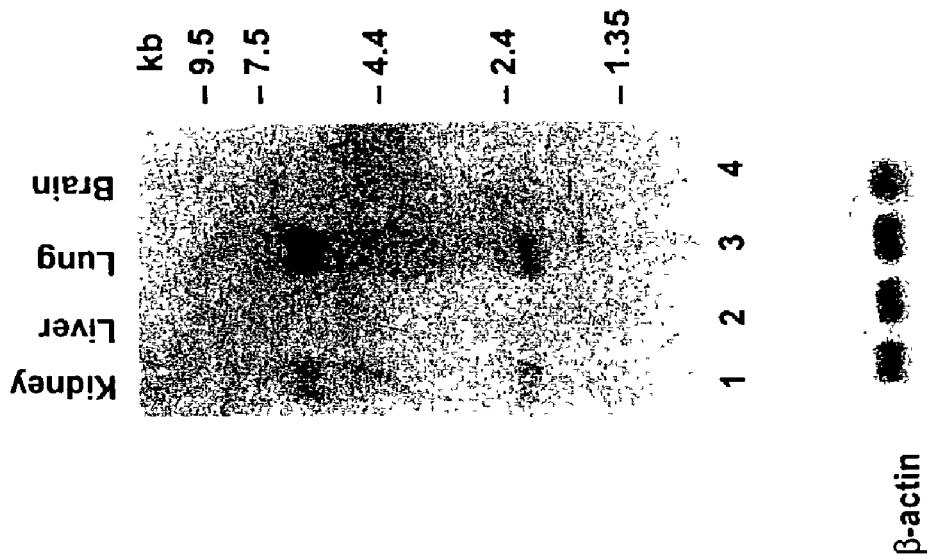
FIG. 3B is an autoradiogram showing the results of Northern blot of fetal tissue, using the same probe as described in FIG. 3A
Figure 3A:
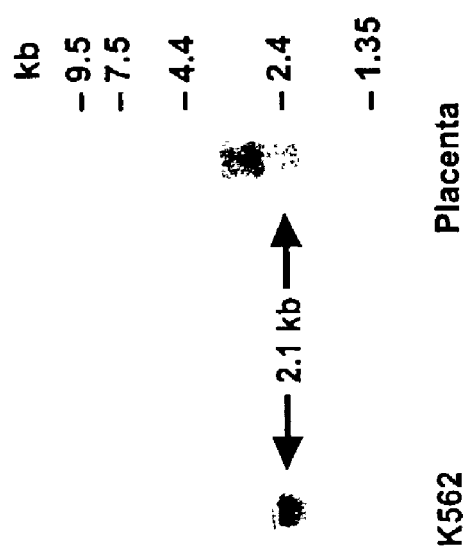
FIG. 3A is an autoradiogram showing the results of a Northern blot of K562 RNA using part of the 630 bp BP1 cDNA (obtained as described herein) as a probe. An RNA band of 2.1 kb was recognized.

The BP1 cDNA obtained was 630 bp in length. When part of this sequence was used as a probe in a Northern blot containing K562 RNA, an RNA band of 2.1 kb was recognized (FIG. 3A). This result indicated an incomplete cDNA had been cloned. To extend the cDNA sequence, rapid amplification of cDNA ends (RACE) was used. Additional sequences in both the 5' and 3' directions were obtained, giving a cDNA of 1366 bp. Subsequently fine-tuning led to the 1251 bp sequence of SEQ ID:1 (and FIG. 4). Further, the predicted open reading frame (ORF) was obtained.

Computer analysis using BLAST indicated that BP1 contains a homeobox (HB), placing it in a family of genes known to be important in development. Several sub-families of homeobox genes have been defined. BP1 is a member of the Distal-less (Dlx) family, based on sequence homology to the homeobox of these genes. In FIG. 4, the homeobox is underlined and the amino acids comprising the three predicted α helices found in homeodomains (see, for example, Pabo, C. O. and R. T. Sauer. 1992. Transcription factors: structural families and principles of DNA recognition. Annu. Rev. Biochem. 61: 1053–1095.) are also indicated. The second and third helices comprise the helix-turn-helix (HTH) motif which is characteristic of homeodomains. A putative translational start site was determined by homology with the Kozak consensus sequence (see, for example, Kozak, M. 1987. An analysis of 5'-noncoding sequences from 699 vertebrate messenger RNAs. Nucl. Acids Res. 15: 8125–8148). The open reading frame (ORF) and its predicted amino sequence are shown.

Figure 5B:
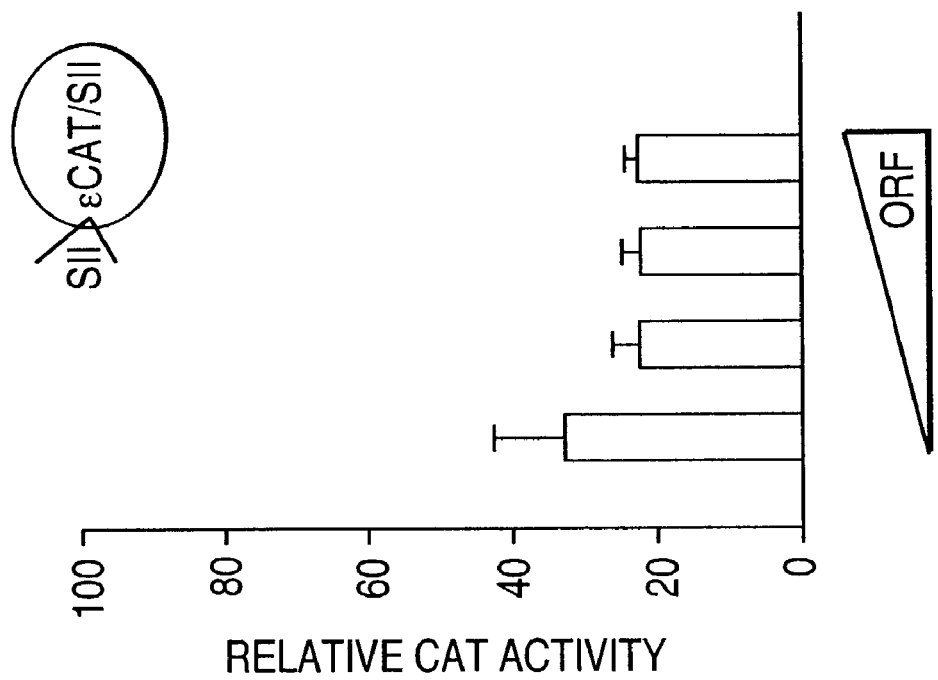
FIG. 5A and FIG. 5B are graphs showing the relative CAT activity of K562 cells in transient transfection assays in relation to increasing amounts of pRSV/BP1-ORF (subcloned as described herein) or to an empty vector.
Figure 5A:
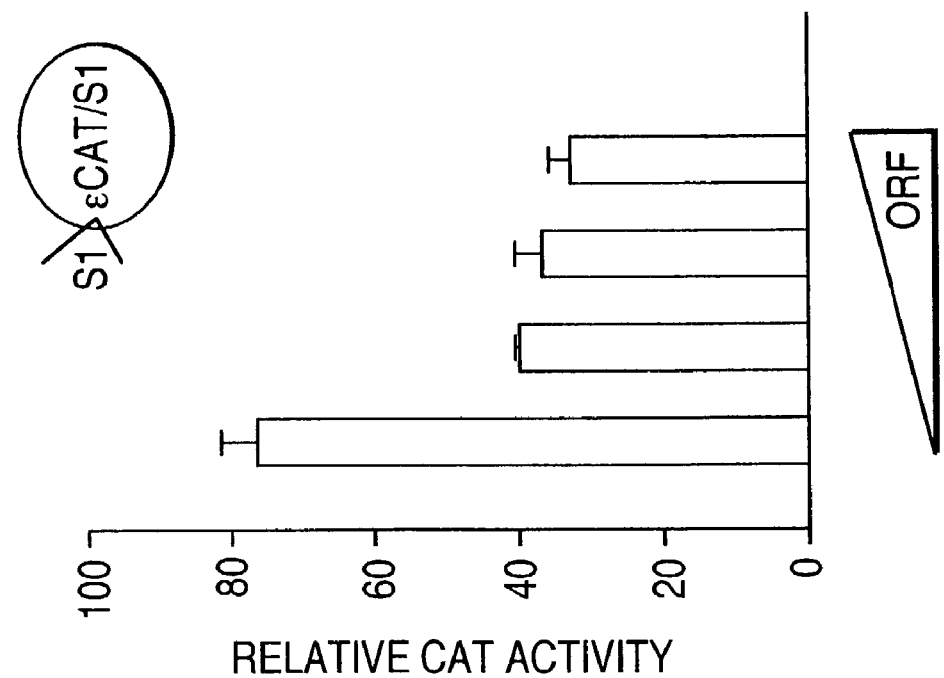

Transient Transfection Assays:

To examine the function of the cloned BP1 ORF, transient transfection assays were performed. The open reading frame (ORF) described above was sub-cloned to create pRSV/BP1-ORF. K562 cells were transiently co-transfected with increasing amounts of either an empty vector or pRSV/BP1-ORF, along with a target plasmid (FIGS. 5A and 5B). The target DNA consisted of Silencer I (peCAT/SI) or Silencer II (peCAT/SII) cloned into an expression vector containing the epsilon globin promoter fused to the CAT reporter gene. (This plasmid was originally used in experiments which defined Silencers I and II (see, for example, Berg, P. E., D. M. Williams, R.-L. Qian, R. B. Cohen, S. X. Cao, M. Mittelman, and A. N. Schechter. 1989. A common protein binds to two silencers 5' to the human β-globin gene. Nucl. Acids Res. 17: 8833–8852). CAT activity was normalized against a co-transfected internal standard, pCMV/βgal. Relative CAT activity was calculated as the ratio of CAT activity in cells receiving pRSV/BP1-ORF to the CAT activity of cells receiving only the empty vector. When increasing amounts of pRSV/BP1-ORF DNA were added to peCAT/SI (FIG. 5A), CAT activity was repressed in a dose dependent manner, with a plateu beginning at 3 µg of pRSV/BP1-ORF. Likewise, increasing addition of pRSV/BP1-ORF DNA to pegCAT/SII caused increasing repression of the CAT reporter gene (FIG. 5B), but the lowest amount added, 1 µg, caused a sharp decrease in CAT expression. A control, an eCAT plasmid lacking silencer DNA, was unresponsive to the addition of pRSV/BP1-ORF (data not shown). Thus, it was shown that BP1 exhibits repressor activity towards both silencers of the β-globin gene.

Expression Analysis of BP1:

Northern analysis was performed to determine the pattern of BP1 expression in human tissues and cell lines. In placenta, the BP1 probe recognized three bands, of 2.1, 2.6 and 3.2 kb (FIG. 3A). A Northern blot of fetal tissue was also probed, with the results shown in FIG. 3B. There was expression in both fetal kidney and lung (lanes 1 and 3), with bands of 2.1 and 6.3 kb, while no expression was detected in fetal liver or brain (lanes 2 and 4). The 2.1 kb band likely corresponds to BP1, since it is the sole band in K562 cells from which BP1 was cloned. The other bands may represent additional isoforms, commonly associated with homeobox genes (see, for example, Cohen, S. M. and G. Jurgens. 1989. Proximal-distal pattern formation in *Drosophila*: cell autonomous requirement for Distal-less gene activity in limb development. EMBO J 8: 2045–2055; Lowney, P., J. Corral, M. M. LeBean, L. Deaven, H. J. Lawrence, and C. Largman. 1991. A human Hox1 homeobox gene exhibits myeloid-specific expression of alternative transcripts in human hematopoietic cells. Nucl. Acids Res. 19: 3443–3449. and O'Connor, M. B., R. Binari, L. A. Perkins, and W. Bender. 1988. Alternative RNA products from the Ultrabithorax domain of the bithorax complex. EMBO J 7: 435–445.)

To analyze expression in a broad spectrum of tissues, a dot blot containing normal human RNA from 50 tissues was probed (Table 1, below). Strong expression was seen in placenta and kidney, and weak expression was observed in cerebral cortex, spleen, mammary gland, small intestine, lung, fetal lung and fetal kidney (the latter two being present on both the Northern blot of FIG. 3B and the RNA dot blot). RNA from 41 additional tissues showed no expression.

TABLE 1

Tissue specific expression of BP1

| Strong | Weak | Negative | Negative |
|---|---|---|---|
| placenta | cerebral cortex | whole brain | thyroid gland |
| kidney | spleen | amygdala | salivary gland |
|  | mammary gland | caudate nucleus | pituitary |
|  | small intestine | cerebellum | gland trachea |
|  | lung | hippocampus | peripheral |
|  | fetal lung | frontal lobe | leukocyte |
|  | fetal kidney | medulla oblongata | lymph node |
|  |  | occipital lobe | bone marrow |
|  |  | putamen | appendix |
|  |  | substantia nigra | thalamus |
|  |  | temporal lobe | liver |
|  |  | subthalamic | spinal cord |
|  |  | nucleus | fetal spleen |
|  |  | thymus | fetal thymus |
|  |  | heart | fetal brain |
|  |  | aorta | fetal heart |
|  |  | skeletal muscle | fetal liver |
|  |  | colon |  |
|  |  | bladder |  |
|  |  | uterus |  |
|  |  | prostate |  |
|  |  | stomach |  |
|  |  | testis |  |
|  |  | ovary |  |
|  |  | pancreas |  |
|  |  | adrenal gland |  |

Figure 6:
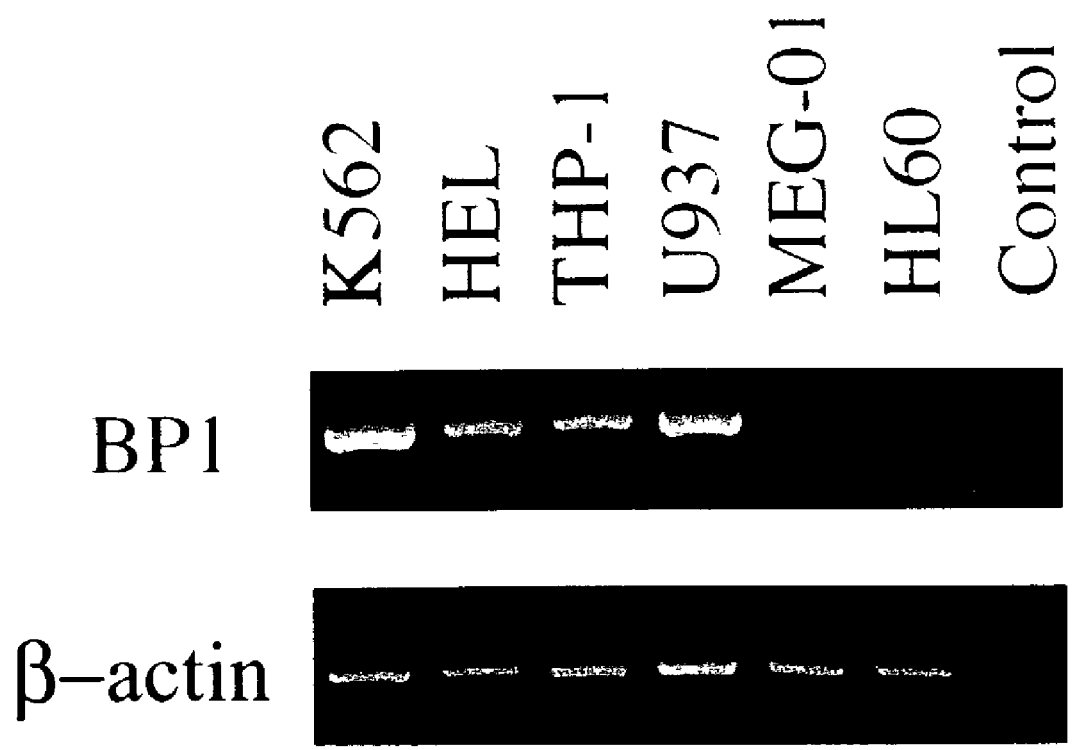
FIG. 6 is an autoradiogram showing the expression of BP1 in erythroid and myeloid lineage cell lines, as determined by RT-PCR.

Thus far, twenty-five human homeobox genes belonging to the HOX family have been described that are expressed during normal hematopoietic development and in leukemic cell lines, often in a lineage-specific manner (see, for example, Lawrence, H. J. and C. Largman. 1992. Homeobox genes in normal hematopoiesis and leukemia. Blood 80: 2445–2453). Therefore, the expression of BP1 in erythroid and myeloid lineage cell lines were examined by RT-PCR (FIG. 6). The strongest expression was seen in erythroid K562 and HEL cells and monocytic THP-1 and U937 cells, with less expression in megakaryocytic MEG-01 cells and monocytic/granulocytic HL60 cells. Although the cell lines used in this experiment are often examined for expression of genes in hematopoietic lineages, it should be noted that they are derived from leukemias.

As described above, BP1 exhibits repressor function. Using increasing amounts of a plasmid containing the ORF causes increasing repression of a target εCAT reporter gene containing Silencer I or II DNA. Expression of the reporter genes was not completely extinguished, which is believed to be due to a possible requirement for binding of additional, low abundance repressor proteins. One such protein may be BP2, which also binds to Silencer II DNA and appears to have repressor function (Berg, P. E., D. M. Williams, R.-L. Qian, R. B. Cohen, S. X. Cao, M. Mittelman, and A. N. Schechter. 1989. A common protein binds to two silencers 5' to the human β-globin gene. Nucl. Acids Res. 17: 8833–8852 and Ebb, D., D. C. Tang, L. Drew, K. Chin, P. E. Berg, and G. P. Rodgers. 1998. Identification of regulatory elements that repress adult beta-like globin genes. Blood Cells, Mol., Dis. 24: 356–369.). The data and the fact that an intact BP1 binding site is required for Silencer II function (see, for example, Ebb, D., D. C. Tang, L. Drew, K. Chin, P. E. Berg, and G. P. Rodgers. 1998. Identification of regulatory elements that repress adult beta-like globin genes. Blood Cells, Mol., Dis. 24: 356–369.) shows that BP1 is most likely a repressor of the β-globin gene. As such, it is the first β-globin repressor to be cloned.

BP1 is a homeobox gene and a member of the Distal-less family (see, for example, Cohen, S. M., G. Bronner, F. Kuttner, G. Jurgens, and H. Jackle. 1989. Distal-less encodes a homeodomain protein required for limb development in *Drosophila*. Nature 338: 432–434.). Homeobox genes are known as master regulator genes during development because, upon mutation, vast morphologic abnormalities occur. Distal-less genes are found in organisms as diverse as mice, *Xenopus*, zebrafish and humans (see, for example, Stock, D. W., D. L. Ellies, Z. Zhao, M. Ekker, F. H. Ruddle, and K. M. Weiss. 1996. The evolution of the vertebrate Dlx family. Proc. Natl. Acad. Sci. USA 93: 10858–10863). In *Drosophila*, Distal-less (called Dll) is required for the normal development of larval sensory organs of the head and thorax. In larval and adult flies, Dll plays an important role in the development of the distal regions of the limbs (see, for example, Cohen, S. M. and G. Jurgens. 1989. Proximal-distal pattern formation in Drosophila: cell autonomous requirement for Distal-less gene activity in limb development. EMBO J 8: 2045–2055 and Cohen, S. M., G. Bronner, F. Kuttner, G. Jurgens, and H. Jackle. 1989. Distal-less encodes a homeodomain protein required for limb development in *Drosophila*. Nature 338: 432–434.). There is a single Dll gene in *Drosophila*, but multiple Distal-less genes in other organisms. In mammals, seven Distal-less (called Dlx in mammals) genes have been identified so far. During murine development, Dlx genes are expressed in branchial arches, forebrain, limbs, eyes, teeth, bones and facial mesenchyme (see, for example, Dolle, P., M. Price and D. Duboule. 1992. Expression of the murine Dlx-1 homeobox gene during facial, ocular, and limb development. Differentiation 49: 93–99, Robinson, G. W. and K. Mahon. 1994. Differential and overlapping expression domains of Dlx-2 and Dlx-3 suggest distinct roles for Distal-less homeobox genes incraniofacial development. Mech. Dev. 48: 199–215 and Simeone, A., D. Acampora, M. Pannese, M. D'Esposito, A. Stornaiuolo, M. Gulisano, A. Mallamaci, K. Kastury, T. Druck, and K. Huebner. 1994. Cloning and characterization of two members of the vertebrate Dlx gene family. Proc. Natl. Acad. Sci. USA 91: 2250–54).

BP1 and two recently discovered human genes, DLX7 (see, for example, Nakamura, S., D. W. Stock, K. L. Wydner, J. A. Bollekens, K. Takeshita, B. M. Nagai, S. Chiba, T. Kitamura, T. M. Freeland, Z. Zhao, J. Minowada, J. B. Lawrence, K. B. Weiss, and F. H. Ruddle. 1996. Genomic analysis of a new mammalian Distal-less gene: Dlx-7. Genomics 38: 314–324) and DLX4 (formerly called Dlx8; see, for example, Quinn, L. M., B. V. Johnson, J. Nicholl, G. R. Sutherland, and B. Kalionis. 1997. Isolation and identification of homeobox genes from human placenta including a novel member of the Distal-less family, Dlx4. Gene 187: 55–61) appear to be isoforms, since their homeoboxes are identical and they exhibit extensive areas of homology. Using fluorescence in situ hybridization, BP1 was mapped to chromosome 17q21-23, also the locus of DLX7 and DLX4. Further, BP1 and DLX7 (see, for example, Nakamura, S., D. W. Stock, K. L. Wydner, J. A. Bollekens, K. Takeshita, B. M. Nagai, S. Chiba, T. Kitamura, T. M. Freeland, Z. Zhao, J. Minowada, J. B. Lawrence, K. B. Weiss, and F. H. Ruddle. 1996. Genomic analysis of a new mammalian Distal-less gene: Dlx-7. Genomics 38: 314–324 and Price, J. A., D. W. Bowden, J. T. Wright, M. J. Pettenati, and T. C. Hart. 1998. Identification of a mutation in Dlx3 associated with tricho-dento-osseous (TDO) syndrome. Hum. Mol. Gen. 7: 563–569) share complete sequence identity from nucleotides 565 to 1250 of BP1 while, further upstream of nt 565, there is no homology. Sequence homology between BP1 and DLX4 also begins at nt 565 of BP1 and includes the homeobox. The functions of DLX7 and DLX4 are not known. However, abrogation of DLX7 expression in K562 cells causes apoptosis (see, for example, Shimamoto, T., S. Nakamura, J. Bollekens, F. H. Ruddle and K. Takeshita. 1997. Inhibition of Dlx-7 homeobox gene causes decreased expression of GATA-1 and c-myc genes and apoptosis. Proc. Natl. Acad. Sci. USA 94: 3245–3249). Preliminary data suggests lack of BP1 causes apoptosis in K562 cells.

A striking feature of BP1 is its restricted expression. BP1 mRNA is most strongly expressed in placenta and kidney (Table 1 and FIG. 3). Although no homeobox sequences were present in the probe, there was partial sequence homology to DLX7. Thus, expression of BP1 in placenta and bone marrow by RT-PCT was assessed using BP1-specific primers; a band of the correct size was observed. The seven tissues exhibiting weak hybridization may be expressing BP1 and/or DLX7.

Forty-one tissues lacked BP1 expression. It seemed surprising that BP1 mRNA was absent in fetal liver and fetal spleen, if BP1 represses adult globin gene expression. However, both of these tissues were obtained from 24 week fetuses, by which time β-globin expression has already begun (see, for example, Ley, T. J., K. A. Maloney, J. I. Gordon and A. L. Schwartz. 1989. Globin gene expression in erythroid human fetal liver cells. J. Clin. Invest. 83: 1032–1038, Mavilio, F., A. Giampaolo, A. Care, G. Migliaccio, M. Calandrini, G. Russo, G. L. Pagliardi, G. Mastroberardino, M. Marinucci, and C. Peschle. 1983. Molecular mechanisms of human hemoglobin switching: selective undermethylation and expression of globin genes in embryonic, fetal, and adult erythroblasts. Proc. Nat. Acad. Sci. USA 80: 6907–6911, and Papayannopoulou, T., T. H. Shepard, and G. Stamatoyannoupoulos.1983. Studies of hemoglobin expression in erythroid cells of early human fetuses using anti-γ- and anti-β-globin chain fluorescent antibodies, p. 421–430. In G. Stamatoyannopoulos and A. W. Nienhuis (ed.), Globin Gene Expression and Hematopoietic Differentiation. Alan R. Liss, New York). To examine this point further, RT-PCR was performed on four 10 week fetal liver samples. Even by 10 weeks, β-globin transcription has begun (see, for example, Ley, T. J., K. A. Maloney, J. I. Gordon and A. L. Schwartz. 1989. Globin gene expression in erythroid human fetal liver cells. J. Clin. Invest. 83: 1032–1038) and BP1 expression using 30 cycles of amplification samples were not detected; at 35 cycles a detectable band of the correct size in each of the four was observed. Thus, there are very low amounts of BP1 in fetal liver; yolk sac tissue is not available to better trace its pattern of expression.

At least 25 HOX genes, the largest family of human homeobox genes, are expressed during hematopoietic development, often in a lineage-specific manner (reviewed in Lawrence, H. J. and, C. Largman. 1992. Homeobox genes in normal hematopoiesis and leukemia. Blood 80: 2445–2453. However, the functions of these genes are unknown. The identification of BP1 as a regulator of the β-globin gene makes this the first human homeobox gene with a known function in hematopoiesis.

In addition to the Silencer I and Silencer II binding sites discussed above, additional potential gene targets that may be regulated by BP1 have been identified. Sequence analysis was performed to identify DNA sequences with at least 75% homology to known BP1 binding sites. Three sites were identified upstream of the gamma globin genes. These sites are located at –1427 bp and –1091 bp upstream of the Gγ-globin gene and at –1091 bp upstream of the Aγ-globin gene. These sites were shown to be binding sites for BP1 protein using the electrophoretic mobility shift assay.

Creation of a Polyclonal Antibody, Immunoprecipitation and Western Blotting

A polyclonal antibody was raised in rabbits against the unique N-terminal BP1 peptide SYPYTEPANPGDSYLSCQQ (SEQ ID NO:13) (Research Genetics). Freshly prepared K562 cell protein lysate was immunoprecipitated using Protein A Sepharose beads (Biorad). Equal Amounts of K562 protein lysate, immunoprecipitated lysate and cold in vitro transcription/translation protein product were used for analysis by 12.5% SDS-PAGE gel. The proteins were electrophoretcally tranferred to nitrocellulose membranes. BP1 antibody was diluted in PBS (1:2500) and added for 2 hours at room temperature, then the anti-rabbit secondary antibody was added. Detection of the signal was accomplished using an ECL kit according to the recommended protocol (Amersham Pharmacia Biotech)

Creation of a Plasmid Containing Antisense BP1 DNA

A BP1 DNA fragment of 239 bp (nt 219 to 558) was cloned into the vector pMT in an antisense orientation, under control of the sheep metallothionein promoter, as follows. RT-PCR was performed using primers to amplify DNA between nt 219 and nt 1231 of the BP1 cDNA. This fragment was blunt ended and cloned into pGEM7. A 5' BamHI site in the polylinker of pGEM7 and an Xho I site at nt 558 (internal to BP1), were used to release BP1 DNA from the vector. This BP1 fragment of 239 bp was directionally cloned in an antisense orientation into pMT. (see, for example, Canelles, M., Delgado, M. D., Hyland, K. M. Lerga, A., Richard, C., Dang, C. V. and Leon, J. (1997) Max and inhibitory cMyc mutants induce erythroid differentiation and resistance to apoptosis in human myeloid cells. Oncogene 14, 1315–1327.)

Treatment of Sickle Cell Anemia

A mutation in the sixth codon of the beta globin gene causes sickle cell anemia. Current treatments of sickle cell anemia are focused on reactivation of the fetal hemoglobin genes. Such treatments may include gene therapy, which would be used either to replace the beta globin gene or to add a fetal globin gene engineered to overexpress fetal globin protein. However, these treatments are hampered by the presence of the defective sickle cell beta protein, which interferes with the formation of normal hemoglobin.

As discussed above, there are two silencer regions upstream of the β-globin gene and two proteins which bind to them, BP1 and BP2 (see, for example, Berg, P. E., D. M. Williams, R.-L. Qian, R. B. Cohen, S. X. Cao, M. Mittelman, and A. N. Schechter. 1989. A common protein binds to two silencers 5' to the human β-globin gene. Nucl. Acids Res. 17: 8833–8852). BP1 binds within Silencer I at –530 bp relative to the cap site (+1) and within Silencer II at –300 bp, while BP2 binds within Silencer II at –270 bp, shown in FIG. 1. Interestingly, it was found that High Mobility Group Protein I (HMG-I(Y)), an architectural protein, binds to and bends the DNA at or near the BP1 binding site in Silencer I, but not in Silencer II (see, for example, Chase, M. B., S. Haga, W. D. Hankins, D. M. Williams, Z. Bi, J. W. Strovel, C. Obriecht, and P. E. Berg. 1999. Binding of HMG-I(Y) elicits structural changes in a silencer of the human β-globin gene. Am. J. Hem. 60: 27–35). HMG-I(Y) may facilitate binding of BP1 and possibly other repressor proteins in this region. Mutation of the BP1 site in Silencer II partially relieves repression (see, for example, Ebb, D., D. C. Tang, L. Drew, K. Chin, P. E. Berg, and G. P. Rodgers. 1998. Identification of regulatory elements that repress adult beta-like globin genes. Blood Cells, Mol., Dis. 24: 356–369), suggesting that BP1 may act as a repressor of the β-globin gene. Furthermore, BP1 binds in a negative regulatory region upstream of the other adult globin gene, delta (see, for example, Berg, P. E., S. Abhyankar, and M. Chase. 1994. The high mobility group protein HMG-I(Y) binds to a silencer DNA sequence upstream of the human β-globin gene. Blood 84 Suppl 1: 262a). The inventor believes that BP1 coordinately regulates adult globin gene expression.

BP1 protein may be directly involved in the switch from fetal to adult hemoglobin during development since it binds to DNA near the fetal gamma globin genes, as well as near the adult delta and beta globin genes. Experiments have demonstrated that BP1 binding activity is increased upon pharmacologic reactivation of fetal globin genes.

Since BP1 is believed to activate fetal genes while repressing adult genes, it can potentially be used to treat sickle cell anemia, as an alternative to treatments involving adding normal beta gene or gamma gene.

An inverse correlation between the binding affinity of BP1 and the severity of sickle cell anemia (SCA) has been observed (see, for example, Elion, J., P. E. Berg, C. Lapoumeroulie, G. Trabuchet, M. Mittelman, R. Krishnamoorthy, A. N. Schechter, and D. Labie. 1992. DNA sequence variation in a negative control region 5' to the β-globin gene correlates with the phenotypic expression of the β$^s$ mutation. Blood 79: 787–792.). In sickle cell anemia, the mutated β-globin gene (β$^s$) is in strict linkage disequilibrium with five restriction haplotypes (see, for example, Kulozik, A. E., J. S. Wainscoat, G. R. Serjeant, B. D. Kar, B. Al-Awamy, G. J. F. Essan, A. G. Falusi, S. K. Haque, A. M. Hilali, S. Kate, W. A. E. P. Ranasinghe, and D. J. Weatherall. 1986. Geographical survey of β$^s$-globin gene haplotypes: Evidence for an independent Asian origin of the sickle-cell mutation. Am. J. Hum. Genet. 39: 239–244; Lapoumeroulie, C., O. Dunda, G. Trabuchet, M. Mony-Lobe, D. Labie, J. Elion, and R. Krishnamoorthy. 1989. A novel sickle gene of yet another origin in Africa: The Cameroon type. Blood 74: 225a and Pagnier, J., J. G. Mears, O. Dunda-Belkhodja, K. E. Schaefer-Rego, C. Beldjord, R. L. Nagel, and D. Labie. 1984. Evidence of the multicentric origin of the hemoglobin S gene in Africa. Proc. Natl. Acad. Sci. USA 81: 1771–1773.). There are differences in the clinical severity of sickle cell anemia among the haplotypes, with the Indian-Arabo (hereafter referred to as the Indian haplotype) being the mildest and the Bantu the most severely affected (see, for example, Ali, S. A. 1970. Milder variant of sickle cell disease in Arabs in Kuwait associated with unusually high level of foetal haemoglobin. Br. J. Haematol. 19: 613–619 and Perrine, R. P., M. E. Pembrey, S. Perrine, and F. Shoup. 1978. Natural history of sickle cell anemia in Saudi Arabs. A study of 270 subjects. Ann. Internal. Med. 88: 1–6). A sequence polymorphism within the −530 bp binding site for BP1 is also in linkage disequilibrium with these five SCA haplotypes (see, for example, Chebloune, Y., J. Pagnier, G. Trabuchet, C. Faure, G. Verdier, D. Labie, and V. M. Nigon. 1988. Structural analysis of the 5' flanking region of the β-globin gene in African sickle cell anemia patients: further evidence for three origins of the sickle cell mutation in Africa. Proc. Natl. Acad. Sci. USA 85: 4431–4435).

Using electrophoretic mobility shift competition assays, it was found that BP1 binds five to six times more tightly to the Indian haplotype sequence than to the normal or reference sequence (see, for example, Berg, P. E., M. Mittelman, J. Elion, D. Labie, and A. N. Schechter. 1991. Increased protein binding to a −530 mutation of the human β-globin gene associated with decreased β-globin synthesis. Am. J. Hematol. 36:42–47; Elion, J., P. E. Berg, C. Lapoumeroulie, G. Trabuchet, M. Mittelman, R. Krishnamoorthy, A. N. Schechter, and D. Labie. 1992. DNA sequence variation in a negative control region 5' to the β-globin gene correlates with the phenotypic expression of the $\beta^s$ mutation. Blood 79: 787–792 and Zeng, F.-y., G. P. Rodgers, S.-z. Huang, A. N. Schechter, M. Salamah, S. Perrine, and P. E. Berg. 1994. Sequence of the −530 region of the beta globin gene of sickle cell anemia patients with the Arabian haplotype. Human Mutation 3: 163–165). On the other hand, BP1 binds two to three times more weakly to the Bantu haplotype sequence than the reference sequence (see, for example, Elion, J., P. E. Berg, C. Lapoumeroulie, G. Trabuchet, M. Mittelman, R. Krishnamoorthy, A. N. Schechter, and D. Labie. 1992. DNA sequence variation in a negative control region 5' to the β-globin gene correlates with the phenotypic expression of the $\beta^s$ mutation. Blood 79: 787–792), which may allow more transcription of $\beta^s$ resulting in an increased concentration of Hemoglobin S. This correlates with the increased severity of sickle cell disease observed in Bantus.

As stated above, BP1 is a strong candidate for use in therapy of sickle cell anemia (SCA). Decreasing $\beta^s$-globin expression is expected to decrease the intracellular concentration of HbS, in turn decreasing the intracellular HbS concentration and polymer formation, believed to be the primary cause of the clinical effects of SCA (see, for example, Schechter, A. N., C. T. Noguchi and G. P. Rodgers. 1987. Sickle cell disease, p. 179–218. In G. Stamatoyannopoulos, A. W. Nienhuis, P. Leder, Majerus, P. W. (ed.), The Molecular Basis of Blood Diseases. Saunders, Philadelphia). In addition, treatment with a repressor such as BP1 may also indirectly reactivate fetal globin genes. This idea is based on well established observations, both in vivo and in vitro, which demonstrate reciprocal regulation of fetal and adult globin genes. Dover and Boyer (see, for example, Dover, G. J. and S. H. Boyer. 1987. Fetal hemoglobin-containing cells have the same mean corpuscular hemoglobin as cells without fetal hemoglobin: a reciprocal relationship between gamma- and beta-globin gene expression in normal subjects and in those with high fetal hemoglobin production. Blood 69: 1109–1113) demonstrated that reciprocal regulation exists in individuals who express high levels of HbF and low levels of HbA due to SCA, heterocellular hereditary persistence of fetal hemoglobin (HPFH), and β-thalassemia. Perrine et al (see, for example, Perrine, S. P., B. A. Miller, M. F. Greene, R. A. Cohen, N. Cook, C. Shackleton, and D. V. Faller. 1987. Butyric acid analogues augment γ globin gene expression in neonatal erythroid progenitors. Biochem. Biophys. Res. Comm. 148: 694–700.) showed that two factors, α-amino-n-butyric acid and insulin, present in high levels in the plasma of infants born to diabetic mothers, increase γ-globin expression accompanied by decreased β-globin expression. Furthermore, cultured erythroid progenitors from β-thalassemia and SCA patients, when treated with sodium butyrate, 4-phenyl butyrate or phenylacetate exhibited an increase in γ-globin expression and a reciprocal decrease in β-globin expression (see, for example, Fibach, E., P. Prasanna, G. P. Rodgers, and D. Samid. 1993. Enhanced fetal hemoglobin production by phenylacetate and 4-phenylbutyrate in erythroid precursors derived from normal donors and patients with sickle cell anemia and β-thalassemia. Blood 82: 2203–2209 and Perrine, S. P., B. A. Miller, D. V. Faller, R. A. Cohen, E. P. Vichinsky, D. Hurst, B. H. Lubin, and T. Papayannopoulou. 1989. Sodium butyrate enhances fetal globin gene expression in erythroid progenitors of patients with HbSS and β thalassemia. Blood 74: 454–459). Since current treatments of SCA focus on chemical reactivation of fetal globin genes, repression of HbS may reduce or eliminate the need for such chemicals.

As a treatment of sickle cell anemia, the preferred method is to incorporate DNA encoding BP1 into a vector that can be administered to a patient by gene therapy, preferably targeted to tissues that express globin genes. To avoid potential problems caused by overexpression of BP1, the DNA could be linked to a controllable promoter.

Screening of Leukemia

Acute myeloid leukemia (AML) is the second most frequent pediatric leukemia and the most frequent adult leukemia (see, for example, Pui C-H. Childhood leukemias. *New Eng J Med* 1995; 332: 1618–1630 and Karp J E. Acute leukemia: mechanisms of cell survival as targets for therapy. *Int J Oncol* 1997; 11: 657–674.). Survival is poor in AML, with only 30–40% survival in children and 10–35% survival in adults. On the other hand, acute lymphocytic leukemia (ALL) is the most frequent leukemia in children, but is rare in adults. Although several molecular markers have been associated with AML and ALL (see, for example, Look A T. Oncogenic transcription factors in the human acute leukemias. *Science* 1997; 278: 1059–1064; Tenen D G, Hromas R, Licht J D, Zhang D-E. Transcription factors, normal myeloid development and leukemia. *Blood* 1997; 90: 489–491; and Lawrence H J, Sauvageau G, Humphries R K, Largman C. The role of HOX homeobox genes in normal and leukemic hematopoiesis. *Stem Cells* 1996; 14: 281–291), there is clearly a need to identify additional markers which could aid in diagnosis and in determining appropriate therapy, and/or potentially serve as therapeutic targets.

Altered expression of transcription factors, including homeobox genes (HB), has been implicated in acute leukemias, and aberrant expression of homeobox genes has been described Homeobox genes are characterized by a conserved 180 bp DNA sequence encoding the DNA binding domain (see, for example, Levine M, Hoey T. Homeobox proteins as sequence-specific transcription factors. *Cell* 1988; 55: 537–540). They are "master regulator genes" which are extremely important to the physical development of a wide range of organisms. Recent studies have demonstrated that HB genes are also expressed during hematopoiesis (see, for example, Lawrence H J, Sauvageau G, Humphries R K, Largman C. The role of HOX homeobox genes in normal and leukemic hematopoiesis. *Stem Cells* 1996; 14: 281–291). There are several families of HB genes, defined by the extraordinary sequence conservation among their homeoboxes. The largest family, consisting of 39 members in humans, is called HOX.

Some leukemias aberrantly express homeobox genes as fusion proteins (reviewed in Look A T. Oncogenic transcription factors in the human acute leukemias. *Science* 1997; 278: 1059–1064). In these cases, DNA encoding the activation domain from one gene is fused to DNA encoding the DNA binding region of another, bringing a different function to the new protein product. The downstream targets of fusion genes associated with AML or ALL have yet to be determined. In pre-B-cell lymphoblastic leukemia, for example, the HB gene Pbx1 is fused to E2A (see, for example, Lu Q, Wright D D, Kamps M P. Fusion with E2A converts the Pbx1 homeodomain protein into a constitutive transcriptional activator in human leukemias carrying the t(1;19) translocation. *Mol Cell Biol* 1994; 14: 3938–3948) and, in acute myeloid leukemia (AML), HOXA9 is fused to NUP98-HOXA9 (see, for example, Borrow J, Shearman A. M., Stanton Jr. V. P., Becher R, Collins T, Williams A J, Dube I, Katz F, Kwong Y L, Morris C, Ohyashiki K, Toyama K, Rowley J, Housman D E. The t(7;11) (p15;p15) translocation in acute myeloid leukaemia fuses the genes for nucleoporin NUP98 and class I homeoprotein HOXA9. *Nature Genetics* 1996; 12: 159–167 and Nakamura T, Yamazaki Y, Hatano Y, Miura I. NUP98 is fused to PMX1 homeobox gene in human acute myelogenous leukemia with chromosome translocation t(1;11) (q23;p15). *Blood* 1999; 94: 741–747). In other cases of leukemia not involving obvious cytogenetic changes, a gene which is normally silent is either activated or perhaps not downregulated in an early hematopoietic progenitor. This was observed for four of nine HOXB genes which were expressed in T- or B-ALL, but not in normal T or B lymphocytes (see, for example, Petrini M, Quaranta M T, Testa U, Samoggia P, Tritarelli E, Care A, Cianetti L, Valtieri M, Barletta C, Peschle C. Expression of selected human HOX genes in B/T acute lymphoid leukemia and interleukin-2/interleukin-1 β-stimulated natural killer lymphocytes. *Blood* 1992; 80: 185–193).

BP1 expression was investigated in erythromyeloid and lymphoid leukemia cell lines and in bone marrow samples from adult and pediatric acute myeloid leukemia (AML), pediatric acute T-cell lymphocytic leukemia (ALL) and pediatric pre-B-cell ALL. Because there are two apparent isoforms of BP1 called DLX7 and Dlx4, their expression in the same samples was measured. All three are co-expressed in erythroid and monocytic cell lines and in at least half of the lymphoid cell lines. They are barely if at all detectable in normal bone marrow, PHA-stimulated T cells or B cells. BP1 RNA was found in 63% of AML cases, including 81% of the pediatric and 47% of the adult cases, and in 32% of T-ALL cases, but was not expressed in any of the pre-B ALL cases. Similar results were obtained with DLX7 and Dlx4, with co-expression of all three in a significant number of leukemias. The data shows that BP1 expression occurs in early progenitors. The presence of BP1 RNA in leukemic blasts may therefore be a molecular marker for primitive cells and/or may indicate BP1 is an important upstream factor in an oncogenic pathway.

The hypothesis that BP1 is leukemogenic is supported by the present studies showing that overexpression of BP1 causes increases clonogenicity in the cell line K562, as well as causing decreased ability of these cells to undergo erythroid differentiation. Overexpression of BP1 in the erythroeleukemia cell line K562 results in increased growth in soft agar, which is an indicator of leukemogenic potential.

BP1 expression is believed to cause increased proliferation and survival and decreased differentiation in K562 cells. Similar results were found in K562 cells when either of the two well-known oncogenes were overexpressed, c-myc and c-myb. Therefore, the data suggests that BP1 functions as an oncogene in AML and T-cell ALL conditions.

The studies carried out to determine BP1 expression are described in greater detail below:

Materials and Methods:

Culture of leukemic cell lines: T and B-ALL cell lines were grown in RPMI 1640 (Gibco-BRL) supplemented with 2 mM glutamine, 100 U/ml penicillin, 100 µg/ml streptomycin, 0.1 mM non-essential amino acids, 1 mM sodium pyruvate and 10% fetal bovine serum. Erythromyeloid cell lines were cultured in RPMI 1640 supplemented with 2 mM glutamine, 100 U/ml penicillin and 100 µg/ml streptomycin, 10 mM HEPES and 10% fetal bovine serum.

Clinical samples: Normal bone marrows (BM) were obtained from the Brain Tissue Bank for Developmental Disorders at the University of Maryland. Adult AML bone marrow samples were obtained from the University of Maryland Greenebaum Cancer Center and The Johns Hopkins Cancer Center Cytogenetics Core Laboratory. Bone marrow samples from pediatric T and B-ALL patients were obtained from the Pediatric Oncology Group (POG). Informed consent was obtained from each patient or guardian at their local institutions. Leukemia samples contained at least 85% blasts. T and B lymphocytes from peripheral blood of normal donors were obtained by countercurrent elutriation followed by lineage specific separation using magnetic beads (Miltenyi Biotec, Auburn, Calif.).

RT-PCR: Mononuclear cells were isolated for RNA analysis by Ficoll-Paque. Total RNA was extracted from all samples using TRIzol Reagent (Gibco-BRL, Gaithersburg, Md.). For the reverse transcription (RT) reaction, one microgram of DNase I-treated RNA was added to 2.5 µM oligo-d(T) primers (PE Biosystems), 10 U RNase inhibitor (Gibco-BRL), 0.5 mM dNTPs, and 100 U MMLV-reverse transcriptase (Promega). The RT reaction was performed in a thermal cycler at 25° C. for 10 minutes, 4 minutes ramp, 42° C. for 50 minutes, and 99° C. for 5 minutes. One to two microliters of this reaction was used in the PCR reaction. Primers specific for BP1, DLX4 and DLX7 were designed, and the PCR products were verified by restriction enzyme analysis. Linearity assays for each primer set have been performed and cycling conditions adjusted accordingly (data not shown). Primer sequences and PCR cycling conditions are in the following Table 2.

TABLE 2

PCR Primers

| Primers | Sequence | PCR conditions | Product | Reference |
|---|---|---|---|---|
| BP1 | Upper:<br>5'CACCTCCTGTCTTACC<br>CCTACACC3'<br>(SEQ ID NO:8)<br>Lower:<br>5'GCCCTTCCCCAGATTC<br>ACATCATC3'<br>(SEQ ID NO:9) | 94° C./1 min.; 62° C./1 min.;<br>72° C./1.5 min. for 30 cycles | 581 bp | |
| DLX7 | Upper:<br>5'CCTACACCGTGTTGTG<br>CTGC3'<br>(SEQ ID NO:14)<br>Lower:<br>5'CTGTTGCCATAGCCAC<br>TG3'<br>(SEQ ID NO:15) | 94° C./1 min.; 60° C./1 min.;<br>72° C./1.5 min. for 30 cycles | 406 bp | |
| DLX4 | Upper:<br>5'CACGGTGTGGCGGGG<br>GAGACAT3'<br>(SEQ ID NO:16)<br>Lower:<br>5'CTGCGGTGGGAGGTC<br>GGAGTTC3'<br>(SEQ ID NO:17) | 94° C./1 min.; 60° C./1 min.;<br>72° C./1.5 min. for 30 cycles | 350 bp | |
| β-actin | Upper:<br>5'GGATCTTCATGAGGT<br>AGTCAGTC3'<br>(SEQ ID NO:18)<br>Lower:<br>5'CCTCGCCTTTGCCGAT<br>CC3'<br>(SEQ ID NO:19) | 94° C./1 min.; 60° C./1 min.;<br>72° C./1.5 min for 20 cycles | 626 bp | Raff et al, 1996 |
| c-myb | Upper:<br>5'ATTAGGTAATGAATT<br>GTAGCCAG3'<br>(SEQ ID NO:20)<br>Lower<br>5'ACTTAGAGTAATGCTT<br>TTACTGA3'<br>(SEQ ID NO:21) | 94° C./30 sec; 55° C./30 sec.;<br>72° C./1 min. for 28 cycles | 228 bp | Majello et al,<br>1986<br><br>Shimamoto et al,<br>1997 |
| GATA-1 | Upper:<br>5'CCATTGCTCAACTGTA<br>TGGAGGG3'<br>(SEQ ID NO:22)<br>Lower:<br>5'ACTATTGGGGACAGG<br>GAGTGATG3'<br>(SEQ ID NO:23) | 94° C./30 sec; 58° C./30 sec;<br>72° C./1 min. for 28 cycles | 249 bp | Tsai et al, 1989<br><br>Shimamoto et al,<br>1997 |
| SCL | Upper:<br>5'CAATCGAGTGA<br>AGAGGAGACCTCC3'<br>(SEQ ID NO:24)<br>Lower:<br>5'TTGCGGAGCTCGGCA<br>AAGGC3'<br>(SEQ ID NO:25) | 94° C./45 sec; 55° C./45 sec.;<br>72° C./1.5 min for 30 cycles | 144 bp | Chen et al, 1990 |

Semi-quantitative RT-PCR: An oligonucleotide specific for each product was end-labelled with $\gamma$-$^{32}$P-dATP and added to 10 percent of the PCR product (2.5 μl). Hybridization was in the thermal cycler (94° C. for 15 seconds; 42° C. for 1 minute). The hybridized product was electrophoresed on a 5% polyacrylamide gel, the gel was dried, and then exposed to film. The autoradiograph was aligned with the gel and bands were excised and quantitated by scintillation counting.

Expression was scored as negative (−), positive (+) or ambiguous (+/−) by normalizing against β-actin: a ratio was calculated by dividing the cpm in the band representing BP1, DLX7 or DLX4 by the cpm in the β-actin band from the same sample. One normal BM and one remission BM were included in each AML experiment; their ratios (6 repeats of each) averaged 0.01 for BP1, DLX7 and DLX4, and were the guide against which a sample was scored as −(0.0–0.10), +/−(0.11–0.15), +(>0.15) or ++(>0.45). Two phytohemagglutinin (PHA)-stimulated normal T cell cultures were the control for T-cell ALL; their average ratios (10 repeats) were 0.05; the same criteria were used for scoring BP1, DLX7 and DLX4 as above. c-myb and GATA-1 are expressed in normal BM (our observations and also noted in Gewirtz A M, Calabretta B. A c-myb antisense oligodeoxynucleotide inhibits normal human hematopoiesis in vitro. *Science* 1988; 242: 1303–1306. Guerrasio A, Saglio G, Rosso C, Alfarano A, Camaschella C, Lo Coco F, Biondi A, Ranbaldi A, Nicolis S, Ottolenghi S. Expression of GATA-1 mRNA in human myeloid leukemic cells. *Leukemia* 1994; 6: 1034–1038). The average ratios in BM for c-myb and GATA-1 were 0.57 and 2.1, respectively. Samples with a ratio between 0.10 and 1.14 (c-myb) or 0.10 and 4.2 (GATA-1) were scored as (+), i.e., within the range of normal BM, and ratios greater than 1.14 (c-myb) or 4.2 (GATA-1) were scored as (++). Each RT-PCR and hybridization was performed twice, independently.

Isolation of CD34 cells: Bone marrow cells were aspirated from the posterior iliac crest of consenting healthy adult donors following guidelines approved by the Institutional Review Board for NIH. Cells were first prepared with Histopaque-1077 density gradient centrifugation. Mononuclear cells were then incubated with CD34 (QBEnd10)-conjugated magnetic microbeads (AmCellCorp, Sunnyvale, Calif.) and processed through a MACS magnetic separation column (Miltenyi Biotec, Bergisch Gladbach, Germany) to obtain purified CD34+ cells. For higher purity of CD34+ cells, a second column run was used. Purity of isolated CD34+ cells was generally greater than 90%, and cell viability as evaluated by propidium iodide exclusion was always higher than 95%. Purity of the remaining CD34− cells was greater than 95%.

Construction of cell lines overexpressing BP1: A BP1 cDNA fragment of 1013 bp containing the complete open reading frame was amplified by RT-PCR from K562 cell RNA using primers designed from the original cDNA. This fragment was cloned into pGEM7, sequenced, then subcloned into pRC/RSV (Invitrogen) using Hind III and Xba I.

Statistical Analysis: The significance of correlation between expression of BP1, DLX4, and DLX7 was assessed by Fisher's exact test. All p-values reported were two-sided.

Detailed Results:

Expression of BP1 in normal cells: RNA levels for BP1 were determined in four normal bone marrow samples and one bone marrow from an AML patient in remission, and in five PHA-stimulated T-cell and five B-cell preparations from normal bone marrow. Results obtained after semi-quantitative RT-PCR analysis of six representative samples are shown in FIG. 8. BP1 RNA was barely visible in any of these control samples; results were similar for DLX4 and DLX7. After a longer exposure of the autoradiograph, a faint band was seen in all six samples for several of the isoforms (data not shown).

Expression of BP1 in cell lines: Expression of BP1 was examined by RT-PCR in a number of leukemia cell lines. Fourteen cell lines of lymphoid origin were analyzed for BP1 expression. BP1 RNA was present in four of eight T-cell ALL cell lines and in three of four lymphoma cell lines (Table 3).

TABLE 3

Expression of BP1 in Hemopoietic Cell Lines

| | BP1 Expression |
|---|---|
| Lymphoid | |
| B Cell Lineage | |
| Normal ALL | +/− |
| REH | + |
| RS4; 11 | + |
| Burkett's lymphoma | |
| Raji | − |
| Daudi | + |
| T Cell Lineage | |
| Normal ALL | +/− |
| Jurkat | + |
| MOLT-3 | + |
| MOLT-4 | + |
| MOLT-13 | + |
| CCRF-CEM | − |
| HSB2 | − |
| MOLT-16 | − |
| RPMI 8402 | − |
| Lymphoma | |
| HUT78 | + |
| Sup-T1 | + |
| Myeloid | |
| Erythroid | |
| K562 | + |
| HEL | + |
| Monocytic | |
| THP-1 | + |
| U937 | + |
| Megakarycocytic | |
| MEG-01 | +/− |
| Monocytic/granulocytic | |
| HL60 | +/− |

Figure 7A:
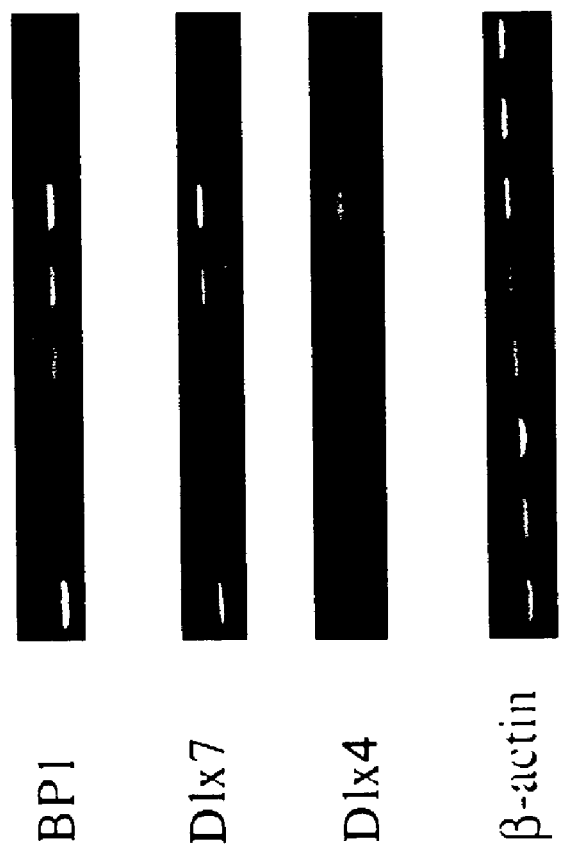
FIGS. 7A and 7B are autoradiograms showing the expression of BP1, DLX7 and DLX4 in T-cell ALL cell lines and erythromyloid cell lines, as determined by RT-PCR.
Figure 7B:
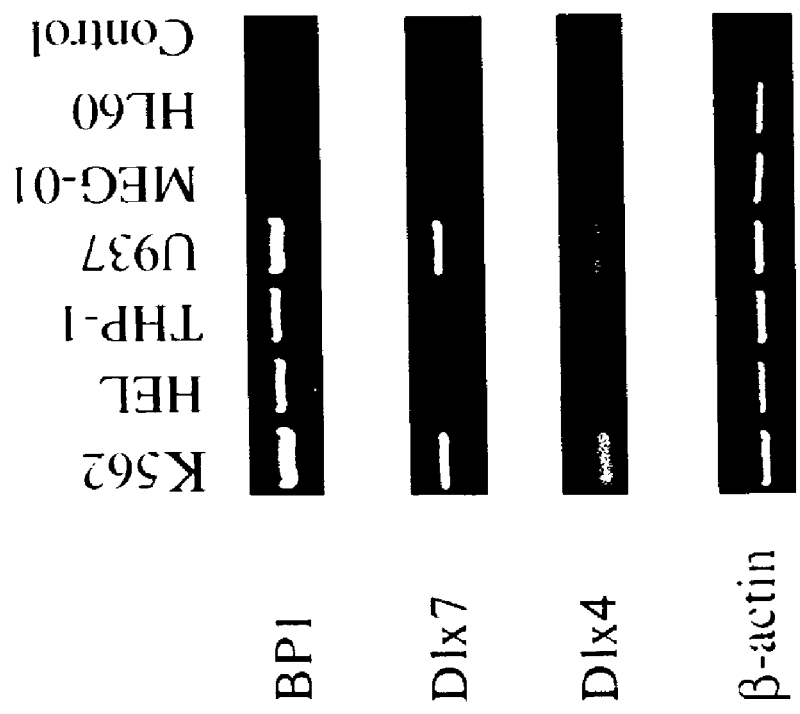

DLX7 and DLX4 RNA levels were also determined in the T-cell ALL cell lines (FIG. 7A), with co-expression of the three isoforms in the same cell lines. BP1 mRNA was also readily detectable in four of six erythromyeloid cell lines (K562, HEL, THP-1 and U937), with less expression in MEG-01 and HL60 cells.[1] Analysis of DLX7 and DLX4 in those cell lines showed that BP1, DLX7 and DLX4 were frequently co-expressed, with greatest expression of all three in K562 and U937 cells (FIG. 7B). The observation that there was little or no expression of any of the isoforms in normal bone marrow (described above), compared with the expression found in diverse myeloid and lymphoid leukemia cell lines, led us to examine the relative expression of BP1, DLX7 and DLX4 in the bone marrow of acute leukemia patients using semi-quantitative RT-PCR.

Expression of BP1 in acute myeloid leukemias: Expression of BP1 was examined in both pediatric and adult AML patients. A total of 39 AML patients were studied, of whom 18 were under the age of 18 (pediatric; cases 8–27) and 21 were 18 years of age or older (adult; cases 29–49). Table 4, below, summarizes the analysis of the AML samples and the clinical data available for each patient, including cytogenetics, expression of surface markers and initial response to treatment; outcome data was not available for all patients and thus was excluded. Data are grouped according to the French-American-British (FAB) criteria. (see, for example, Bennett J M, Catovsky D, Daniel M T, Flandrin G, Galton D A G, Gralnick H R, Sultan C. Proposed revised criteria for the classification of the French-American-British Cooperative Group. *Ann Intern Med* 1985; 103: 620–625. Assignment of expression levels was made as described in Materials and Methods. For this analysis, normal bone marrow was used DLX7 was overexpressed in 59% (10/17) of pediatric and 38% (6/16) of adult cases, while DLX4 was overexpressed in 79% (11/14) of pediatric and 79% (15/19) of adult cases. An example of RT-PCR analysis showing expression in selected samples is seen in FIG. 9. Here, patient 15 showed the greatest BP1 and DLX7 levels, with less DLX4 expression. The correlation between BP1 and DLX7 ($p=0.0002$), BP1 and DLX4 ($p=0.0016$), and DLX7 and DLX4 ($p=0.023$) were statistically significant by Fisher's exact test.

TABLE 4

Expression of BP1, DLX& and DLX4 and clinico-biological features in patients with AML.

| FAB | Patient | BP1 | DLX7 | DLX4 | c-myb | GATA-1 | CD34 | CD33 | CD13 | Karyotype | Response** |
|---|---|---|---|---|---|---|---|---|---|---|---|
| Normal B.M. | | − | − | − | + | + | | | | | |
| M0 | 12* | ++ | + | +/− | ++ | + | − | + | + | ND | PR |
| | 37 | +/− | − | + | ++ | + | + | + | + | 46, XY, t(1, 15), trisomy 1q | NR |
| | 47 | − | − | − | ND | ND | + | + | + | 47, XY, +13 | NR |
| M1 | 15* | ++ | ++ | + | ++ | + | + | + | + | 46, XY, t(11, 9)(q23, p13.1) | CR |
| | 17* | +/− | − | +/− | ++ | + | + | + | + | 46, Y, t(X, 7)(q13, p15), dup(12)(p11p13) | CR |
| | 19* | − | − | − | ++ | + | + | + | + | 46, XX | CR |
| | 22* | ++ | ++ | ++ | +++ | + | + | + | + | 47, XX, +21 | ND |
| | 26* | + | + | +/− | + | + | + | + | + | 46, XX | CR |
| | 27* | − | − | + | + | + | + | + | + | 46, XY | CR |
| | 29 | − | − | + | ++ | + | + | + | + | 46, XY, del(5)(q31q34) | NR |
| | 40 | ++ | ++ | ++ | ++ | +/− | − | + | + | 46, XY, t(1;12) | CTC |
| | 46 | + | + | + | ND | ND | − | + | + | 46, XY, del(1)(q32), del(13)(q12–22) | CR |
| M2 | 18* | + | − | − | +/− | + | + | + | + | 47, XX, +8 | CR |
| | 20* | + | − | + | + | − | − | + | + | 46, XY | CR |
| | 44 | − | ND | +/− | ND | ND | + | + | + | 46, XY | CR |
| | 45 | − | − | − | ND | ND | + | + | − | 45, X, −Y | CR (<6 mo) |
| | 48 | + | +/− | ND | ND | ND | + | + | + | 47, XY, +8 | NR |
| M3 | 41 | + | + | ++ | + | + | − | + | + | 46, XX, t(15, 17)(q21, q12–21) | CR |
| M4 | 23* | +/− | − | − | + | − | + | + | + | 46, XX, inv(16)(p13q22) | CR |
| | 31 | − | − | − | + | + | − | + | + | 45, XY, −7 | NR |
| | 32 | − | − | − | + | + | − | + | + | 45, XX, −16 | NR |
| | 35 | + | +/− | + | + | + | − | + | + | 46, XX | NR |
| | 49 | − | − | + | ND | ND | + | + | + | 46, XY, inv(16)(p13q22) | CR |
| M5 | 8* | + | + | + | ++ | − | − | + | − | 46, XX, t(11, 17)(q23, q25) | CR |
| | 9* | + | +/− | +/− | + | − | − | + | − | ND | CR |
| | 11* | + | + | + | ++ | − | − | + | + | 46, XY | NR |
| | 13* | + | + | + | ++ | + | − | + | − | 46, XY, der(1)t(1, 6)(q32, p21.1), add(11)(q23), der(22)t(1, 22)(q23, q11.2) | CR |
| | 14* | + | + | + | + | + | − | + | + | 46, XX | CR |
| | 16* | + | − | + | + | + | − | + | + | 46, XX | NA |
| | 30 | − | +/− | + | + | − | − | + | + | 47, XY, +3 | NA |
| | 33 | − | − | + | + | + | + | + | + | 46, XY | NR |
| | 34 | + | + | + | + | + | + | + | − | 48, XX, add(4)(p15.1), del(5)(q21q33), t(7, 12)(p10, q10), add(11)(q23), +t(12)(p10), add(16)(q11.2), −17, +18, −20, +der(21)t(17, 21)(q10, q10), +mar | NR |
| | 36 | + | − | + | + | + | + | + | − | 46, XY, del(7)(q22), +(8)(q24.3) | NR |
| | 38 | +/− | − | + | + | + | + | + | + | 46, XX | CR |
| | 39 | − | +/− | ++ | + | + | − | + | + | 48, XY, t(1;16), +7, +19 | CTC |
| | 42 | + | + | + | + | − | 13% | + | 62% | 47, XY, t(6, 9)(q23, q34), +8 | RD |
| | 43 | + | + | + | ND | ND | − | + | + | 46, XY, t(3, 5)(q25, q34) | NR |
| M7 | 21* | + | ++ | ++ | +++ | +++ | + | + | − | 46, XY | CR |
| | 24* | + | + | + | ++ | + | + | + | + | 45, XY, t(3, 3)(q21, q26), −7 | NR |

*AGE LESS THAN 18
**COMPLETE RESPONSE(CR),
NO RESPONSE (NR),
PARTIAL RESPONSE (PR),
COMPLETE TUMOR CLEARANCE (CTC)
RESIDUAL DISEASE(RD),
NOT DETERMINED (ND),
DATA NOT AVAILABLE(NA)

as a negative baseline against which the clinical samples were compared. Samples classified as +/− were excluded from statistical analysis. BP1 was overexpressed in a definitive manner in 81% (13/16) of the pediatric bone marrow samples and in 47% (9/19) of the adult cases.

Analysis of GATA-1 and c-myb, markers of primitive cells, was performed on the AML samples to indicate the differentiation state of cells expressing BP1. GATA-1 is believed to be involved in positive regulation of myeloid development and thought to be expressed in early progenitors, then downregulated in myeloid (but not erythroid) differentiation, making its expression in the myeloid pathway a sign of immaturity.(see, for example, Crotta S, Nicolis S, Ronchi A, Ottolenghi S, Ruzzi L, Shimada Y, Migliaccio A R. Progressive inactivation of the expression of an erythroid transcriptional factor in GM- and G-CSF-dependent myeloid cell lines. *Nucl Acids Res* 1990; 18: 6863–6869) It is detected in acute leukemias characterized by expansion of early progenitors.(see, for example, Guerrasio A, Saglio G, Rosso C, Alfarano A, Camaschella C, Lo Coco F, Biondi A, Ranbaldi A, Nicolis S, Ottolenghi S. Expression of GATA-1 mRNA in human myeloid leukemic cells. *Leukemia* 1994; 6: 1034–1038) c-myb is expressed in immature hematopoietic cells, and its expression decreases as cells differentiate.(see, for example, Gewirtz A M, Calabretta B. A c-myb antisense oligodeoxynucleotide inhibits normal human hematopoiesis in vitro. *Science* 1988; 242: 1303–1306; Gonda T, Metcalf D. Expression of myb, myc and fos proto-oncogenes during the differentiation of a murine myeloid leukemia. *Nature* 1984; 310: 249–251 and Luscher B, Eisenman R N. New light on Myc and Myb. Part II. Myb. *Genes & Devel* 1990; 4: 2235–2241.) Since c-myb and GATA-1 are expressed in normal bone marrow (data not shown), (see, for example, Gewirtz A M, Calabretta B. A c-myb antisense oligodeoxynucleotide inhibits normal human hematopoiesis in vitro. *Science* 1988; 242: 1303–1306 and Guerrasio A, Saglio G, Rosso C, Alfarano A, Camaschella C, Lo Coco F, Biondi A, Ranbaldi A, Nicolis S, Ottolenghi S. Expression of GATA-1 mRNA in human myeloid leukemic cells. *Leukemia* 1994; 6: 1034–1038.) A classification of positive was given to samples expressing c-myb at the level of normal cells (see above for details). It was found that every AML sample exhibited c-myb expression at least equal to that in normal bone marrow, and 42% (13/31) exhibited greater expression. A higher proportion of pediatric than adult cases showed high level c-myb expression, 59% in children compared with 21% in adults. GATA-1 was present in 77% (24/31) of AML cases, with 72% expression in children and 85% in adults.

Co-expression of DLX7 and DLX4 with BP1 was striking: 84% of BP1+ samples were DLX7+ and 100% were DLX4+. GATA-1 was co-expressed in 74% of the samples, and all were c-myb positive, with 45% exhibiting high levels of c-myb. Another parameter in this study was analysis of surface markers. Interestingly, 64% of the BP1 positive samples were CD34 negative, while 73% were CD13 positive and 100% were CD33 positive.

Among the 39 AML patients, two had an abnormal chromosome 17q arm, the locus of BP1. (see, for example Fu S, Strovel J W, Haga S B, Stamberg J, Berg P E. Mapping of a new homeobox gene, BP1, near its isoform DLX7 and characterization of their roles in repression of the beta globin gene. *Am. J. Hum. Gen.* 1998; 63: A181.) Patient 41, with acute promyelocytic leukemia, exhibited a t(15;17) translocation presumably involving the retinoic acid receptor on chromosome 17.(see, for example, Look A T. Oncogenic transcription factors in the human acute leukemias. *Science* 1997; 278: 1059–1064) Patient 8 exhibited a t(11;17)(q23;q25) translocation. This translocation has been identified as fusing the MLL gene on chromosome 11q23 to either the AF17q25 gene or to MSF, both located on 17q25 and differing by a single base. (see, for example, Baer M R, Stewart C C, Lawrence D, Arthur D C, Mrozek K, Strout M P, Davey F R, Schiffer C A, Bloomfield C D. Acute myeloid leukemia with 11q23 translocations: myelomonocytic immunophenotype by multiparameter flow cytometry. *Leukemia* 1998; 12: 317–325; Taki T, Ohnishi H, Shinohara K, Sako M, Bessho F, Yanagisawa M, Hayashi Y. AF17q25, a putative septin family gene, fuses the MLL gene in acute myeloid leukemia with t(11;17)(q23;q25). *Cancer Res* 1999; 59: 4261–4265 and Osaka M, Rowley J D, Zeleznik-Le N J. MSF (MLL septin-like fusion), a fusion partner gene of MLL, in a therapy-related acute myeloid leukemia with a t(11;17) (q23;q25). *Proc Natl Acad Sci USA* 1999; 96: 6428-6433.) Since the MLL gene is known to activate several HOX genes,(see, for example, Yu B D, Hess J L, Horning S E, Brown G A J, Korsmeyer S. Altered Hox expression and segmental identity in M11-mutant mice. *Nature* 1995; 378: 505–508.) it is tempting to speculate that the fusion protein may activate BP1 in this case.

Expression of BP1 in acute lymphoid leukemias: For comparison with the myeloid lineage leukemias, nineteen cases of pediatric T-cell ALL were examined (Table 5).

TABLE 5

Expression of BP1, DLX7 and DLX4 in Children with T-Cell ALL

| Patent | BP1 | DLX7 | DLX4 |
|---|---|---|---|
| 1 | − | − | − |
| 2 | − | + | − |
| 3 | − | + | − |
| 4 | + | − | − |
| 5 | + | + | + |
| 6 | − | − | − |
| 7 | − | + | + |
| 8 | − | − | − |
| 9 | − | − | − |
| 10 | + | + | + |
| 11 | − | nd | − |
| 12 | + | − | − |
| 13 | − | − | + |
| 14 | + | + | + |
| 15 | − | nd | nd |
| 16 | + | + | + |
| 17 | − | nd | nd |
| 18 | − | nd | nd |
| 19 | − | nd | nd |

Figure 10:
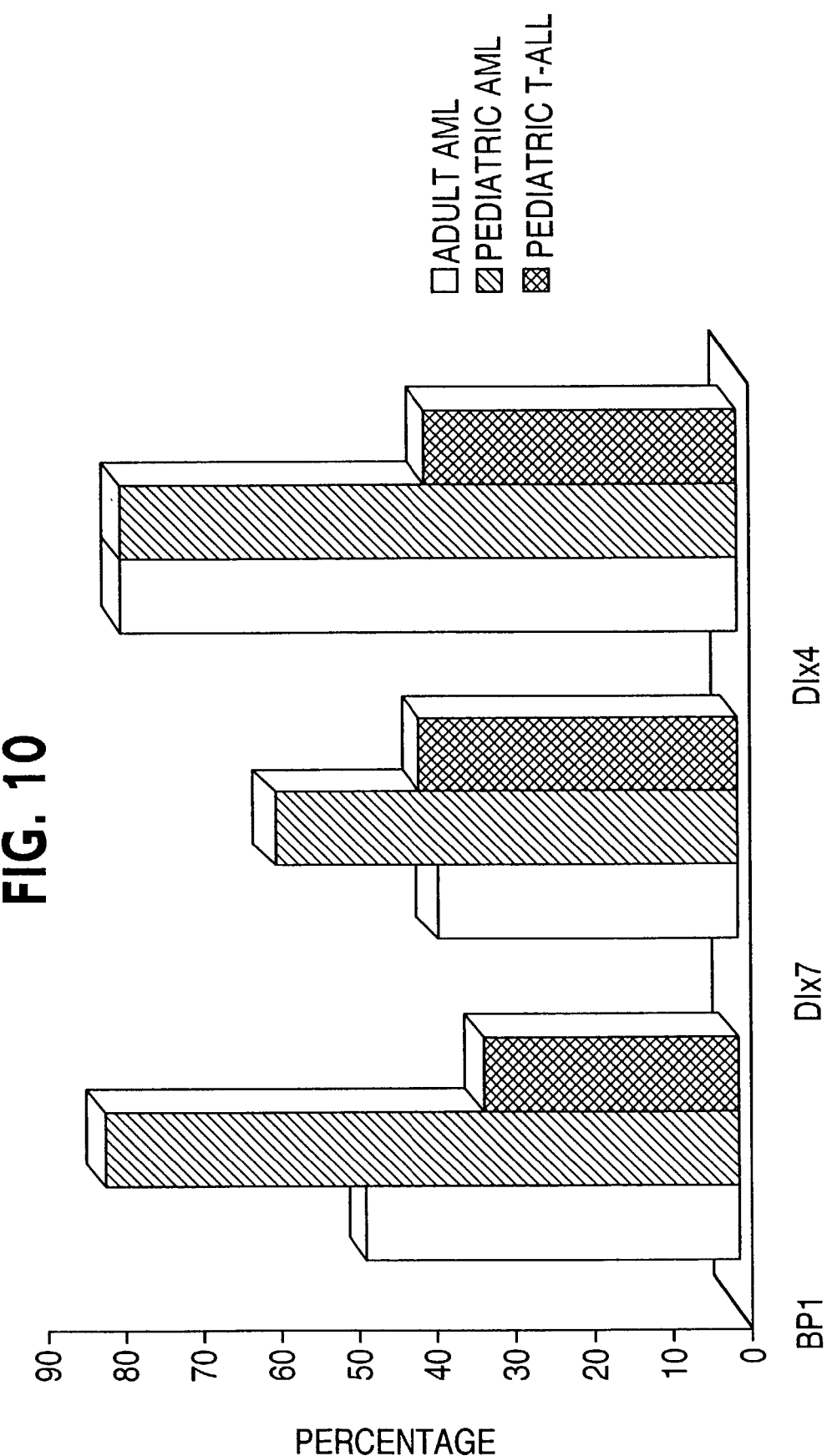
FIG. 10 is a graph comparing the expression of BP1, DLX7 and DLX4 in AML and T-cell ALL. Black bars represent adult AML, and white bars represent pediatric T-cell ALL.

Here, 32% (6/19) were BP1 positive. Outcome data were not available for these patients. Analysis of DLX7 and DLX4 showed that 40% of the cases were DLX7 positive, and 40% (6/15) were DLX4 positive. A comparison of expression of the three isoforms in AML and T-cell ALL is seen in FIG. 10.

Next, 19 pediatric patients with pre B-ALL were analyzed. No detectable BP1 was observed in any of these cases, although the β-actin controls were normally expressed (data not shown).

Figure 11:
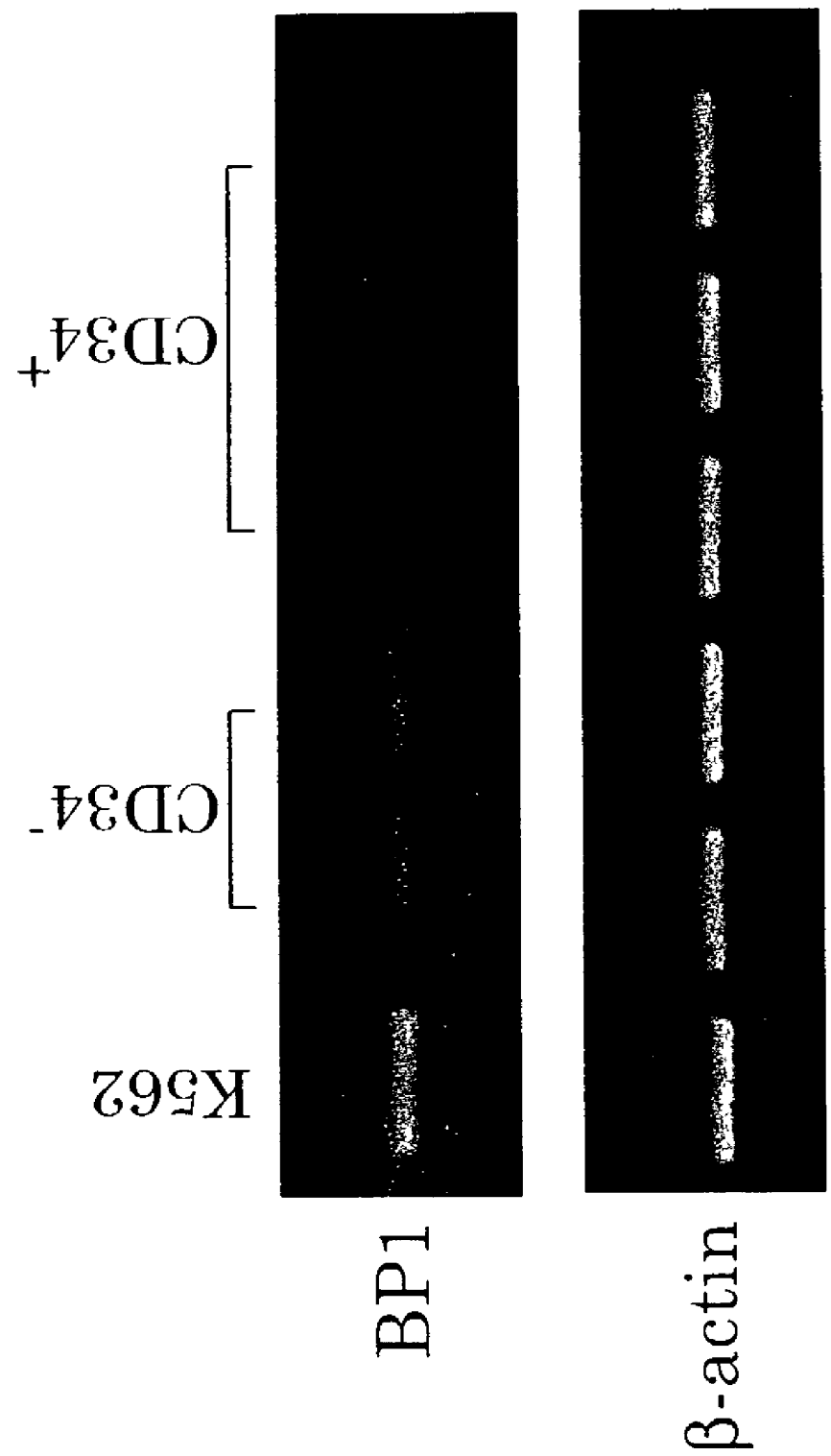
FIG. 11 is an autoradiogram showing BP1 expression in $CD34^+$ and $CD34^-$ cells.

BP1 expression in CD34+ and CD34− cells: To examine more precisely the reason for very low BP1 expression in normal bone marrow and to determine whether BP1 is expressed in early progenitors, BP1 expression was measured in CD34+ and CD34− cells. There was clear expression in two independent isolates of CD34− cells (FIG. 11, lanes 2 and 3). In contrast, there was barely detectable BP1 mRNA in three independent samples of CD34+ bone marrow (lanes 4, 5 and 6). Expression in K562 cells is shown for comparison in lane 1, and b-actin was measured as a loading control.

Clonogenicity of K562 cells overexpressing BP1: It has been found that enforced expression of BP1 in K562 cells leads to decreased differentiation and increased clonogenicity. The human erythroleukemia cell line K562 was used to examine the effects of ectopic BP1 expression on erythroid differentiation. Four independent K562 clones overexpressing BP1 were isolated and compared with two clones containing an empty vector. All of the overexpressing cell lines were found to exhibit a diminished ability to undergo erythroid differentiation (data not shown).

Clonogenicity, considered to be a measure of oncogenicity, can be measured by the ability of leukemia cells to grow in 0.5% soft agar. Three of the cell lines overexpressing BP1 exhibited significantly increased numbers of colonies able to grow in soft agar per 15,000 cells plated compared with controls (Table 6, below). These results suggest BP1 overexpression may be associated with increased oncogenicity in K562 cells and may increase proliferative capacity or cell survival. The average number of cells per colony (an indicator of proliferation) was determined by pooling 30 colonies to obtain an average number of cells per colony (Table 6).

This number did not increase in the overexpressing cell lines, and the proliferation curves were the same for the overexpressing cell lines and the controls (data not shown), making it likely that the overexpressors show increased survival relative to 7a and 7b rather than increased proliferation. Taken together, these data imply that BP1 expression may direct K562 cells towards survival at the expense of differentiation, a characteristic exhibited by some oncogenes.

TABLE 6

Clonogenicity of K562 cells overexpressing BP1

| Cell Line plated | Relative BP1 Expression | Col./15,000 | Avg. no. cells/colony |
| --- | --- | --- | --- |
| 7a (control) | 1 | 23 ± 15 | 4400 |
| 7b (control) | 1 | 21 ± 7 | 1300 |
| 8a | 21 | 517 ± 108 | 2900 |
| 8c | 12 | 924 ± 199 | 5300 |
| 8d | 5 | 223 ± 34 | 5800 |
| 8e | 7 | 57 ± 18 | 2300 |

K562 cells are BCL-2 negative, p53 negative and contain the BCR-ABL translocation; the effects of overexpressing BP1 in K562 cells occur against this transformed background. For this reason, NIH 3T3 cells, which are immortalized but not transformed (they do not cause malignancy if injected into mice), were used. Enforced expression of BP1 in those cells led to increased growth in soft agar, but at a reduced level of about 4-fold. NIH 3T3 cells overexpressing BP1 also exhibited about a 4-fold increase in focus formation. The difference in the effect of high BP1 expression on K562 cells and NIH 3T3 cells may mean that additional genetic changes are required for the approximately 10-fold larger increase in clonogenicity seen in K562 cells.

Discussion:

To summarize, significant RNA expression of BP1 was detected in the bone marrow of 81% of pediatric AML patients, compared with 47% of adult patients. In contrast, expression of BP1 was not reproducibly found in normal bone marrow. The highest percentage of BP1 positives occurred in the FAB classification M5 (monocytic), in which 77% of AML cases were BP1 positive; bone marrow cells from 100% of the children in this category were BP1 positive. Two splice variants, DLX7 and DLX4, were co-expressed in 48% and 79% of AML patients, respectively. BP1, DLX7 and DLX4 levels were also assessed in 19 cases of pediatric T-cell ALL. Although the frequency of expression was less in comparison with AML, BP1 was overexpressed in 32%, DLX7 in 50% and DLX4 in 40% of T-cell ALLs, compared with weak or no expression in normal PHA-stimulated T lymphocytes. In sharp contrast, no BP1 expression was detected in pre-B ALL. Although the reason for expression of BP1 in T-cell ALL but not in pre B-cell ALL is not obvious, this difference may provide a useful diagnostic distinction.

c-myb was expressed in all AML samples, either at a level comparable to normal bone marrow or at a higher level. Expression of c-myb is associated with immaturity, (see, for example, Gewirtz A M, Calabretta B. A c-myb antisense oligodeoxynucleotide inhibits normal human hematopoiesis in vitro. *Science* 1988; 242: 1303–1306; Gonda T, Metcalf D. Expression of myb, myc and fos proto-oncogenes during the differentiation of a murine myeloid leukemia. *Nature* 1984; 310: 249–251 and Luscher B, Eisenman R N. New light on Myc and Myb. Part II. Myb. *Genes & Devel* 1990; 4: 2235–2241.) so those cases within the normal range may be arrested at an early progenitor stage. Higher c-myb expression may be part of the leukemogenic process since activation of c-myb causes leukemia in mice.(see, for example, Wolff L, Koller R, Bies J, Nazarov V, Hoffman B, Amanullah A, Krall M, Mock B. Retroviral insertional mutagenesis in murine promonocytic leukemias: c-myb and Mml1. *Curr Topics Micro Immuno* 1996; 211: 191–199.) In this regard, of 11 samples which highly expressed c-myb and could be evaluated for BP1 expression, 9 were BP1 positive. There is a substantial body of data on expression of HOX genes in malignant hematopoietic cell lines. The HOX genes are clustered on four chromosomes, and the DLX genes are located in pairs on the same chromosomes.(see, for example Lawrence H J, Sauvageau G, Humphries R K, Largman C. The role of HOX homeobox genes in normal and leukemic hematopoiesis. *Stem Cells* 1996; 14: 281–291 and van Oostveen J W, Biji J J, Raaphorst F M, Walbooners J J M, Meijer C J L M. The role of homeobox genes in normal hematopoiesis and hematological malignancies. *Leukemia* 1999; 13: 1675–1690; Nakamura S, Stock D W, Wydner K L, Bollekens J A, Takeshita K, Nagai B M, Chiba, Kitamura T, Freeland T M, Zhao Z, Minowada J, Lawrence J B, Weiss K B, and Ruddle F H. Genomic analysis of a new mammalian Distal-less gene: Dlx-7. *Genomics* 1996; 38: 314–324.; Simeone A, Acampora D, Pannese M, D'Esposito M, Stornaiuolo A, Gulisano M, Mallamaci A, Kastury K, Druck T, Huebner K. Cloning and characterization of two members of the vertebrate Dlx gene family. *Proc Natl Acad Sci USA* 1994; 91: 2250–2254.) BP1 is situated at the 3' end of the HOXB cluster on chromosome 17. (see, for example Fu S, Strovel J W, Haga S B, Stamberg J, Berg P E. Mapping of a new homeobox gene, BP1, near its isoform DLX7 and characterization of their roles in repression of the beta globin gene. *Am. J. Hum. Gen.* 1998; 63:A181.) HOXB genes are preferentially expressed in erythroid cells, including K562 and HEL cell lines.(see, for example, Lawrence H J, Sauvageau G, Humphries R K, Largman C. The role of HOX homeobox genes in normal and leukemic hematopoiesis. *Stem Cells* 1996; 14: 281–291; Shen W-F, Largman C, Lowney P, Corral J C, Detmer K, Hauser C A, Simonitch T A, Hack F M, Lawrence H J. Lineage-restricted expression of homeobox-containing genes in human hematopoetic cell lines. *Proc Natl Acad Sci USA* 1989; 86: 8536–8540; Magli C M, Barba, P, Celetti A, De Vita G, Cillo, C, Boncinelli E. Coordinate regulation of HOX genes in human hematopoietic cells. *Proc Natl Acad Sci USA* 1991; 88: 6348–6352; and Mathews C H E, Detmer K, Boncinelli E, Lawrence H J, Largman C. Erythroid-restricted expression of homeobox genes of the human HOX2 locus. *Blood* 1991; 78: 2248–2252). It is believed that genes in the HOX clusters are switched off or on in blocks in myeloid cells. (see, for example, 38, 40) The data presented herein suggest that BP1 may be part of this coordinate regulation since its pattern of expression in erythromyeloid cell lines is similar to that of the adjacent HOXB genes. Transcripts of HOX genes have also been found in AML, T-ALL and pre B-ALL but, unlike BP1, they are readily detectable in normal bone marrow. (see, for example, Petrini M, Quaranta M T, Testa U, Samoggia P, Tritarelli E, Care A, Cianetti L, Valtieri M, Barletta C, Peschle C. Expression of selected human HOX genes in B/T acute lymphoid leukemia and interleukin-2/ interleukin-1 β-stimulated natural killer lymphocytes. *Blood* 1992; 80: 185–193; Lawrence H J, Sauvageau G, Ahmadi N, Lopez A R, LeBeau M M, Link M, Humphries K, Largman C. Stage- and lineage-specific expression of the HOXA10 homeobox gene in normal and leukemic hematopoietic cells. *Exp Hem* 1995; 23: 1160–1166; Biji J J, van Oostveen J W, Walboomers J M M, Brink A T P, Vos W, Ossenkoppele G J, Meijer C J L M. Differentiation and cell-type-restricted expression of HOXC4, HOXC5 and HOXC6 in myeloid leukemias and normal myeloid cells. *Leukemia* 1998; 12: 1724–1732; Kawagoe H, Humphries R K, Blair A, Sutherland H J, Hogge D E. Expression of HOX genes, HOX cofactors, and MLL in phenotypically and functionally defined subpopulations of leukemic and normal human hematopoietic cells. *Leukemia* 1999; 13: 687–698; Salvati P D, Ranford P R, Ford J, Kees U R. HOX11 expression in pediatric acute lymphoblastic leukemia is associated with T-cell phenotype. *Oncogene* 1995; 11: 1333–1338) Notably, the expression of HOX genes is downregulated during normal hematopoietic differentiation but not in AML.(see, for example, Kawagoe H, Humphries R K, Blair A, Sutherland H J, Hogge D E. Expression of HOX genes, HOX cofactors, and MLL in phenotypically and functionally defined subpopulations of leukemic and normal human hematopoietic cells. *Leukemia* 1999; 13: 687–698). BP1 RNA expression in acute leukemias may represent a marker for the differentiation stage of the leukemic blasts and/or may be directly involved in leukemogenesis. The data presented herein point to the possibility that BP1 expression in AML occurs in early progenitors: (i) As described above, all of the BP1 positive cells are also c-myb positive and 74% are GATA-1 positive, two indicators of early progenitors. (see, for example, 20,22–24 (ii) The barely detectable expression of BP1 seen in normal bone marrow is compatible with expression in primitive cells, which comprise a very small sub-population of normal bone marrow. (iii) Overexpression of BP1 in both myeloid and lymphoid leukemia argues that leukemogenesis may occur in a stem cell or multipotent hematopoietic progenitor. (iv) Further supporting this idea is the observation that 59% of BP1 positive blasts are found in FAB classes considered to be primitive and associated with stem cell leukemias, i.e., MO (minimally differentiated), M5 (monocytic) or M7 (megakaryocytic). (see, for example, Cuneo A, Mecucci C, Kerim S, Vandenberghe E, Dal Cin P, Van Orshoven A, Rodhain J, Bosly A, Michaux J L, Martiat P., Boogaerts M, Carli MG, Castoldi G, Van Den Berghe H. Multipotent stem cell involvement in megakaryoblastic leukemia: cytologic and cytogenetic evidence in 15 patients. *Blood* 1989; 74: 1781–1790; Bonnet D, Dick J E. Human acute leukemia is organized as a hierarchy that originates from a primitive hematopoietic cell. *Nature Medicine* 1997; 3: 730–737; Venditti A, Del Poeta G, Buccisano F, Tamburini A, Cox M C, Stasi R, Bruno A, Aronica G, Maffei L, Suppo G, Simone M D, Forte L, Cordero V, Postorino M, Tufilli V, Isacchi G, Masi M, Papa G, Amadori S. Minimally differentiated acute myeloid leukemia (AML-MO): Comparison of 25 cases with other French-American-British subtypes. *Blood* 1997; 89: 621–629.) (v) 64% of BP1 positive cases are CD34 negative. CD34+ stem cells express several HOX genes, and this expression is down-regulated in CD34– cells.(see, for example, van Oostveen J W, Biji J J, Raaphorst F M, Walbooners J J M, Meijer C J L M. The role of homeobox genes in normal hematopoiesis and hematological malignancies. *Leukemia* 1999; 13: 1675–1690 and Sauvageau G, Lansdorp P M, Eaves C J, Hogge D E, Dragowska W H, Reid D S, Largman C, Lawreence J, Humphries R K. Differential expression of homeobox genes in functionally distinct CD34+ subpopulations of human bone marrow cells. *Proc Natl Acad Sci USA* 1994; 91: 12223–12227.) In contrast, BP1 is expressed in CD34-cells and down-regulated in CD34+ cells. These results are in agreement with the data in AML samples (point v), in which BP1 was primarily found in CD34– cells. The very low expression in CD34+ cells could represent either expression in a few CD34+ cells or contamination of the CD34+ cells with CD34– cells. Recent papers support the existence of a sub-population of primitive CD34– lin– stem cells with repopulating ability in both mice and humans. (see, for example, 49-51 In mice, CD34– lin– stem cells can convert to CD34+ stem cells upon activation); this has not been investigated in humans. (see, for example, Goodell M A. CD34+ or CD34–: does it really matter? *Blood* 1999; 94: 2545–2547 and Sato T, Laver J H, Ogawa M. Reversible expression of CD34 by murine hematopoietic stem cells. *Blood* 1999; 94: 2548–2554). Since our CD34-cells contain both lin+ and lin-subpopulations, it is not known whether BP1 is expressed in stem cells. However, it is clear that BP1 is activated early in hematopoesis. It is therefore hypothesized that that BP1 expression is then repressed during differentiation. This idea is strengthened by the observation that BP1 is down-regulated during erythroid differentiation of the cell line MB-02. In support of a possible oncogenic role for BP1, it was observed that stable cell lines overexpressing BP1 exhibited up to a 45-fold increase in clonogenicity. Moreover, its high frequency of expression in AML may indicate BP1 is an upstream factor in an oncogenic pathway. Further experiments are needed to delineate the roles of BP1 in normal hematopoiesis, to directly determine if it plays a role in neoplastic transformation, and to examine the clinical significance of its expression in acute leukemias.

In view of the above findings of increased expression of BP1 in leukemias, a method of screening for acute myeloid leukemia or acute lymphocytic leukemia includes the steps of obtaining a cell sample from a patient and determining whether BP1 is overexpressed by cells in the cell sample, as compared to normal cells. Typically, to test for leukemias, the cell sample is taken from appropriate sources such as bone marrow or peripheral blood. The determination of whether BP1 is overexpressed is preferably carried out by measuring BP1 RNA levels or BP1 protein levels in a cell sample. RNA levels can be determined by RNA assays known in the art such as Northern blot analysis, slot and dot blot analysis, RT-PCR and in situ hybridization. For example, the technique of reverse transcription polymerase chain reaction (RT-PCR), such as in the typical examples described above, can be used to determine whether cells are producing BP1 RNA. Specifically, RNA is isolated from the sample cells and transcribed to obtain a reverse-transcription product (cDNA). A polymerase chain reaction is then carried out using forward and reverse PCR primers derived from SEQ ID NO:1. Suitable PCR primer pairs for BP1 include, for example, SEQ ID NOs 8 and 9, which amplify a product of 581 bp and SEQ ID NOs 10 and 11, which amplify a product of 225 bp. The polymerase chain reaction is carried out under any suitable reaction conditions for amplifying the BP1 product. For example, for the primers of SEQ ID NOs 8 and 9, typical reaction conditions comprise a denaturation step (94° C., 1 min), an annealing step (58°, 1 min) and an elongation step (72° C., 1.5 min) for 27 cycles, followed by an additional extension (72° C., 5 min). For the primers of SEQ ID NOs 10 and 11, typical reaction conditions comprise holding the sample at 94° C. for 2 minutes; then carrying out 30 cycles of 94° C. for 1 minute, 62° C. for 1 minute and 72° C. for 1.5 minutes, 30 cycles; and then holding the sample at 72° C. for 10 minutes. The PCR products are then separated from the sample and visualized or quantified by typical methods such as electrophoresis. BP1 protein levels may be measured directly by protein assays known in the art such as immunohistochemical assays. To provide polyclonal or monoclonal antibodies for immunoassays, the BP1 DNA disclosed herein can be used, by techniques known in the art, to produce sufficient quantities of substantially purified BP1 to use to innoculate a mammal to produce polyclonal or monoclonal antibodies that bind specifically to BP1.

Treatment of Leukemia

Figure 12:
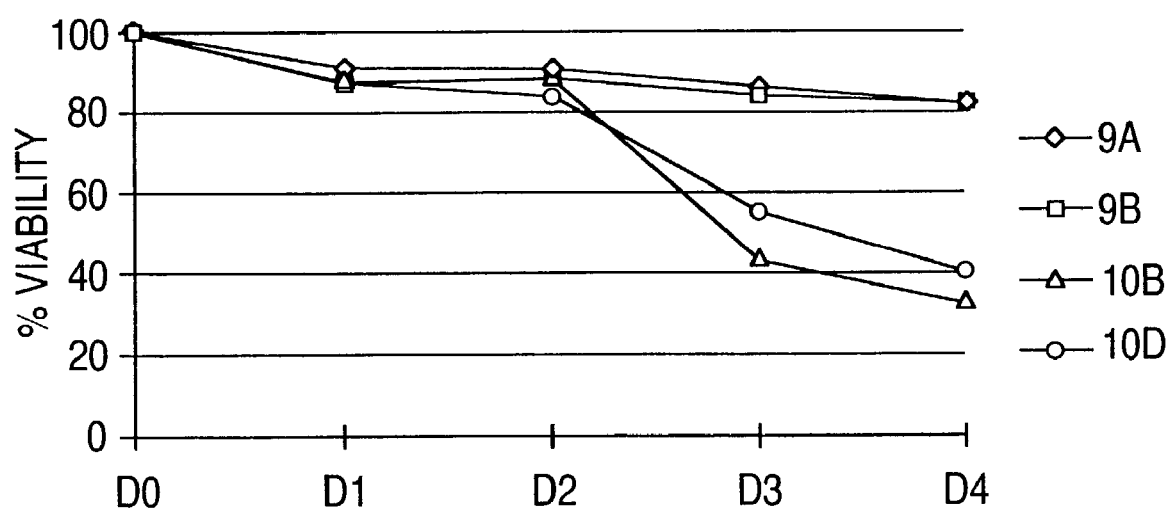
FIG. 12 is a graph showing the percent viability over the course of four days of cell lines transformed with an BP1 antisense-producing plasmid (10B and 10D) in comparison with control cells receiving an empty vector (9A and 9B).
Figure 13:
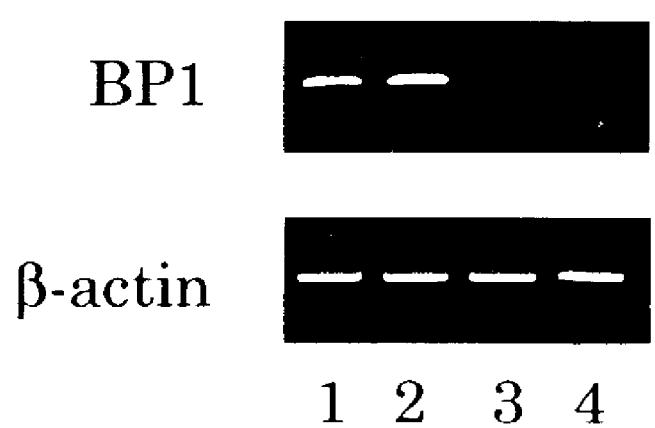
FIG. 13 is an autoradiogram showing BP1 expression of the cell lines 9A–9B receiving an empty vector (lanes 1–2) and cell lines transformed with an BP1 antisense-producing plasmid 10B–10D (lanes 3–4).

Decreasing the BP1 expression in K562 leukemia cells causes apoptosis. To demonstrate this, a vector containing an inducible metallothionein promoter regulating antisense BP1 expression was constructed and stably introduced it into K562 cells. Four cell lines were studied, two controls containing an empty vector (9A and 9B) and two containing the antisense plasmid (10B and 10D). CdSO$_4$, an inducer of the metallothionein promoter, was added at 50 μM for up to four days to induce antisense BP1 expression. Induction of antisense BP1 led to loss of viability, measured by trypan blue (FIG. 12). There was some loss of viability of the controls, but significantly greater cell death for 10B and 10D. This correlated with a great reduction of BP1 mRNA at this time. FIG. 13 shows the expression of BP1 mRNA assessed by RT-PCR for the controls, 9A and 9B (lanes 1 and 2, respectively), compared with 10B and 10D (antisense, lanes 3 and 4, respectively) in the presence of 50 μM CdSO$_4$. BP1 RNA expression is almost extinguished in 10B and 10D. To determine whether loss of viability was due to increased apoptosis, cells were assessed using Annexin V and scored for Annexin V positive, propidium iodide negative cells; apoptosis of the antisense-containing cells significantly increased (data not shown). These experiments indicate that decreasing BP1 expression is associated with apoptosis and, in conjuction with the fact that cells overexpressing BP1 appear to exhibit increased survival, confirm that modulation of BP1 expression has strong consequences for cell survival in K562 cells.

TABLE 7

Percent apoptosis of K562 cells after induction of BP1 antisense RNA

| Cell Line | Day 1 | Day 2 | Day 3 |
|---|---|---|---|
| 9A | 9 ± 1 | 7 ± 3 | 13 ± 3 |
| 9B | 5 ± 3 | 9 ± 1 | 13 ± 1 |
| 10B | 6 ± 1 | 15 ± 2 | 53 ± 4 |
| 10D | 9 ± 1 | 20 ± 1 | 68 ± 1 |

These results suggest that a possible treatment for leukemia may be to introduce antisense oligonucleotides of the DNA encoding BP1 into a patient whereby the antisense oligonucleotides block the expression of BP1 in leukemia cells, thereby causing apoptosis of these cells.

It has also been found that enforced expression of BP1 causes increased sensitivity of leukemia cells to cytosine arabinoside (Ara C), a drug used to treat AML patients. K562 cell lines overexpressing BP1 were challenged with different concentrations of ara C. After challenge with 50 μm ara C for 4 days, the viability of control cells was 82–86% while the viability of cells overexpressing BP1 ranged 27–29% to 66%, i.e., there was up to a three-fold decrease in viability (data not shown). No significant differences in the data were seen at 100 μm Ara C. In an Annexin V assay at 30 minutes and 60 minutes, the highest frequency of apoptotic cells was observed for the cells with the lowest viability. Thus, it is clear that the cell lines with enforced BP1 expression exhibit increased sensitivity to Ara C, evidenced by an increase in apoptosis.

The above findings can be used therapeutically to optimize the dosage of Ara C given to a patient in accordance with the BP1 expression level of that patient.

Screening and Treatment of Breast Cancer

Figure 14:
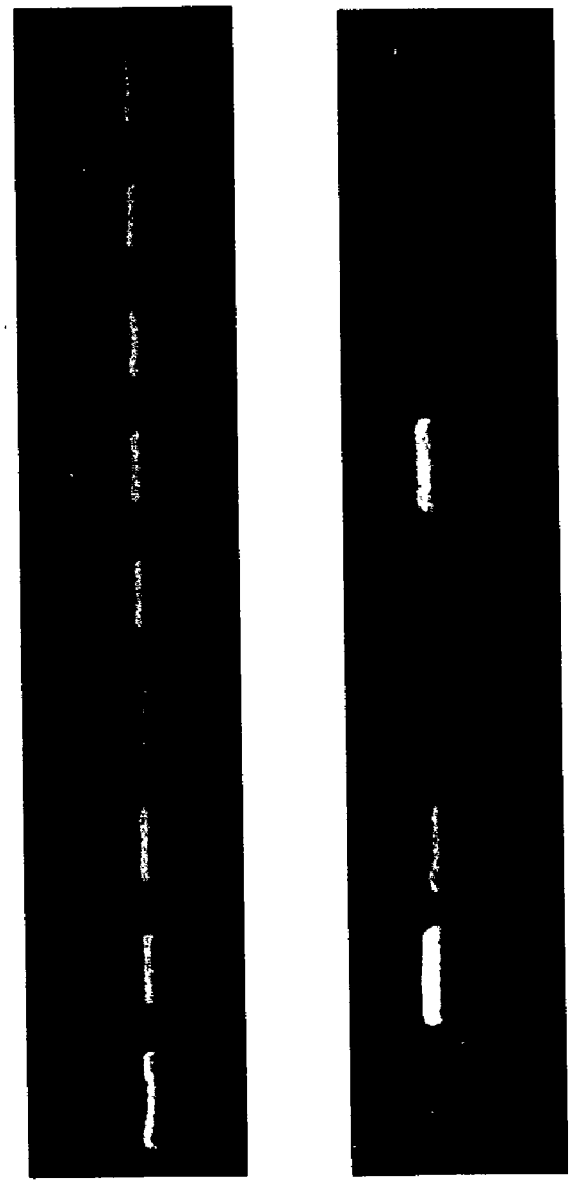
FIG. 14 is an autoradiogram showing the expression of BP1 by several breast cancer cell lines, including breast cancer lines MCF7 ADR, MDA468 and T47D, and no expression in novel breast tissue.

In order to determine whether BP1 is overexpressed in breast cancer cell lines, the inventor conducted studies to detect overexpression of BP1, as compared to normal breast tissue. FIG. 14 shows that expression of BP1 by several breast cancer cell lines, including breast cancer lines MCF7 ADR, MDA468 and T47D. In further studies, BP1 expression was examined by RT-PCR in breast cancer cell lines (Table 8).

TABLE 8

BP1 expression in breast cancer cell lines

| Cell line | ER | PR | Malignancy | Tumorigenic[+] | BP1 |
|---|---|---|---|---|---|
| Hs578T | − | − | ductal ca. | no | +/− |
| MCF7 | + | + | ductal ca. | ** | + |
| MCF7ADR | * | | ADR resistant | yes | +++ |
| MDA-MB-231 | − | − | ductal ca. | yes | ++ |
| MDA-MB-435s | − | − | ductal ca. | no | + |
| MDA-MB-468 | − | − | ductal ca. | yes | ++ |
| T47D | + | + | ductal ca. | NA | +++ |
| MCF10A | + | + | normal | no | +/− |

* non-responsive to estradiol
+ Data from the American Type Culture Collection. NA, data not available.
** Not tumorigenic without the addition of estradiol The most striking correlation was between BP1 expression and the ability of a cell line to cause mammary tumors in mice. Interestingly, high BP1 expression was observed in the adriamycin (ADR) resistant MCF7 cell line, MCF7ADR. Whether there is any relationship between BP1 expression and ADR resistance is unknown. Cell line MCF10A, which is derived from normal breast epithelium, showed barely detectable BP1 mRNA.

To further demonstrate that BP1 is expressed in breast cancer, BP1 expression was examined in frozen breast tumor tissues and in surrounding normal tissue. A total of 15 tumor tissues were analyzed (Table 9). BP1 was expressed in all 12 of the ER negative cases, but in only one of three ER positive cases. These data indicate a trend of BP1 expression in high grade, ER-, PR-tumor tissues.

TABLE 9

Comparison of BP1 expression with ER and PR status in breast cancer

|  | BP1+ | BP1− |
| --- | --- | --- |
| ER+PR+ | 1 | 2 |
| ER−PR− | 12 | 0 |

Figure 15:
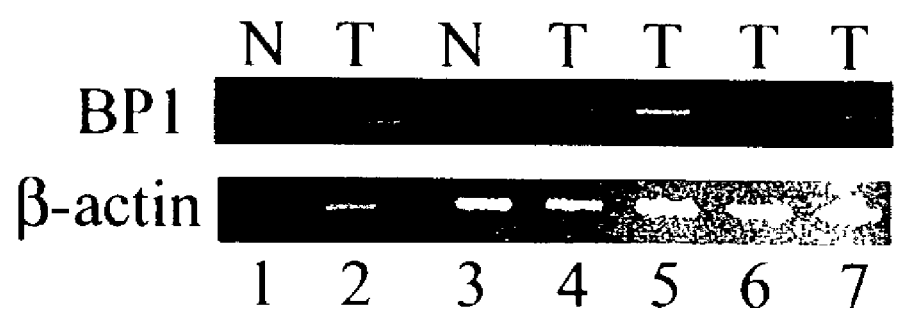
FIG. 15 is an autoradiogram showing the expression of BP1 in normal and malignant breast tissues.

RT-PCR analysis of representative samples from normal and malignant breast tissues are shown in FIG. 15. Normal tissue is indicated by N and tumor by T. All of the tumor tissues shown are ER- PR-. In lanes 1–4, tumor and corresponding normal tissues are shown. No expression was seen for the normal samples, while BP1 was expressed in all of the tumors. A total of six normal breast tissues have been analyzed. Five of the six were BP1 negative and one showed low BP1 expression (data not shown). Three additional tumor tissues are shown in lanes 5–7. β-actin expression demonstrates the integrity of the RNA and serves as a loading control for each sample.

In view of the above, the detection of overexpression of BP1 is a screening tool for breast cancer. The method of screening is carried out in the same manner as the method for screening for leukemia, except that, in the present method, the cell samples are taken from breast tissue.

REFERENCES

Ali, S. A. 1970. Milder variant of sickle cell disease in Arabs in Kuwait associated with unusually high level of foetal haemoglobin. Br. J. Haematol. 19: 613–619.

Berg, P. E., S. Fu, and S. Haga. 1998. Unpublished data. Berg, P. E., S. Abhyankar, and M. Chase. 1994. The high mobility group protein HMG-I(Y) binds to a silencer DNA sequence upstream of the human β-globin gene. Blood 84 Suppl 1: 262a.

Berg, P. E. and A. N. Schechter. 1992. Molecular genetics of disorders of hemoglobin. In T. Friedmann (ed), Molecular Genetic Medicine. Academic Press, San Diego.

Berg, P. E., M. Mittelman, J. Elion, D. Labie, and A. N. Schechter. 1991. Increased protein binding to a −530 mutation of the human β-globin gene associated with decreased β-globin synthesis. Am. J. Hematol. 36: 42–47.

Berg, P. E., D. M. Williams, R.-L. Qian, R. B. Cohen, S. X. Cao, M. Mittelman, and A. N. Schechter. 1989. A common protein binds to two silencers 5' to the human β-globin gene. Nucl. Acids Res. 17: 8833–8852.

Chase, M. B., S. Haga, W. D. Hankins, D. M. Williams, Z. Bi, J. W. Strovel, C. Obriecht, and P. E. Berg. 1999. Binding of HMG-I(Y) elicits structural changes in a silencer of the human β-globin gene. Am. J. Hem. 60: 27–35.

Chebloune, Y., J. Pagnier, G. Trabuchet, C. Faure, G. Verdier, D. Labie, and V. M. Nigon. 1988. Structural analysis of the 5' flanking region of the β-globin gene in African sickle cell anemia patients: further evidence for three origins of the sickle cell mutation in Africa. Proc. Natl. Acad. Sci. USA 85: 4431–4435.

Cho, K. E. Y., J. Geotz, C. V. E. Wright, A. Fritz, A. Hardwicke, and E. M.D. Roberts. 1988. Differential utilization of the same reading frame in a Xenopus homeobox gene encodes two related proteins sharing the same DNA-binding specificity. EMBO J. 7: 2139–2149.

Cohen, S. M. and G. Jurgens. 1989. Proximal-distal pattern formation in Drosophila: cell autonomous requirement for Distal-less gene activity in limb development. EMBO J 8: 2045–2055.

Cohen, S. M., G. Bronner, F. Kuttner, G. Jurgens, and H. Jackle. 1989. Distal-less encodes a homeodomain protein required for limb development in Drosophila. Nature 338: 432–434.

Cowell, I. G. and H. C. Hurst. 199. Cloning transcription factors from a cDNA expression library, p. 120–122. In D. S. Latchman (ed.), Transcription factors: a practical approach. IRL Press, New York.

Crossley, M. and S. H. Orkin. 1993. Regulation of the β-globin locus. Curr. Opinion Gen. Dev. 3: 232–237.

Dignam, J. D., R. M. Lebovitz, and R. G. Roeder. 1983. Accurate transcription initiation by RNA polymerase II in a soluble extract from isolated mammalian nuclei. Nucl. Acids Res. 11: 1475–1489.

Dolle, P., M. Price and D. Duboule. 1992. Expression of the murine Dlx-1 homeobox gene during facial, ocular, and limb development. Differentiation 49: 93–99.

Dover, G. J. and S. H. Boyer. 1987. Fetal hemoglobin-containing cells have the same mean corpuscular hemoglobin as cells without fetal hemoglobin: a reciprocal relationship between gamma- and beta-globin gene expression in normal subjects and in those with high fetal hemoglobin production. Blood 69: 1109–1113.

Ebb, D., D. C. Tang, L. Drew, K. Chin, P. E. Berg, and G. P. Rodgers. 1998. Identification of regulatory elements that repress adult beta-like globin genes. Blood Cells, Mol., Dis. 24: 356–369.

Elion, J., P. E. Berg, C. Lapoumeroulie, G. Trabuchet, M. Mittelman, R. Krishnamoorthy, A. N. Schechter, and D. Labie. 1992. DNA sequence variation in a negative control region 5' to the -globin gene correlates with the phenotypic expression of the s mutation. Blood 79: 787–792.

Fibach, E., P. Prasanna, G.P. Rodgers, and D. Samid. 1993. Enhanced fetal hemoglobin production by phenylacetate and 4-phenylbutyrate in erythroid precursors derived from normal donors and patients with sickle cell anemia and −thalassemia. Blood 82: 2203–2209.

Forrester, W. C., C. Thompson, J. T. Elder, and Groudine, M. 1986. A developmentally stable chromatin structure in the human -globin gene cluster. Proc. Natl. Acad. Sci. USA 83: 1359–1363.

Jaynes, J. B. P. H. and O'Farrell. 1988. Activation and repression of transcription by homeodomain-containing proteins that bind a common site. Nature 336: 744–749.

Kozak, M. 1987. An analysis of 5'-noncoding sequences from 699 vertebrate messenger RNAs. Nucl. Acids Res. 15: 8125–8148.

Kulozik, A. E., J. S. Wainscoat, G. R. Serjeant, B. D. Kar, B. Al-Awamy, G. J. F. Essan, A. G. Falusi, S. K. Haque, A. M. Hilali, S. Kate, W. A. E. P. Ranasinghe, and D. J. Weatherall. 1986. Geographical survey of $\beta^s$-globin gene haplotypes: Evidence for an independent Asian origin of the sickle-cell mutation. Am. J. Hum. Genet. 39: 239–244.

Lapoumeroulie, C., O. Dunda, G. Trabuchet, M. Mony-Lobe, D. Labie, J. Elion, and R. Krishnamoorthy. 1989. A novel sickle gene of yet another origin in Africa: The Cameroon type. Blood 74: 225a.

Lawrence, H. J. and, C. Largman. 1992. Homeobox genes in normal hematopoiesis and leukemia. Blood 80: 2445–2453. Levine, M. and T. Hoey. 1988. Homeobox proteins as sequence-specific transcription factors. Cell 55: 537–540.

Ley, T. J., K. A. Maloney, J. I. Gordon and A. L. Schwartz. 1989. Globin gene expression in erythroid human fetal liver cells. J. Clin. Invest. 83: 1032–1038.

Lowney, P., J. Corral, M. M. LeBean, L. Deaven, H. J. Lawrence, and C. Largman. 1991. A human Hox1 homeobox gene exhibits myeloid-specific expression of alternative transcripts in human hematopoietic cells. Nucl. Acids Res. 19: 3443–3449.

Mavilio, F., A. Giampaolo, A. Care, G. Migliaccio, M. Calandrini, G. Russo, G. L. Pagliardi, G. Mastroberardino, M. Marinucci, and C. Peschle. 1983. Molecular mechanisms of human hemoglobin switching: selective undermethylation and expression of globin genes in embryonic, fetal, and adult erythroblasts. Proc. Nat. Acad. Sci. USA 80: 6907–6911.

Nakamura, S., D. W. Stock, K. L. Wydner, J. A. Bollekens, K. Takeshita, B. M. Nagai, S. Chiba, T. Kitamura, T. M. Freeland, Z. Zhao, J. Minowada, J. B. Lawrence, K. B. Weiss, and F. H. Ruddle. 1996. Genomic analysis of a new mammalian Distal-less gene: Dlx-7. Genomics 38: 314–324.

O'Connor, M. B., R. Binari, L. A. Perkins, and W. Bender. 1988. Alternative RNA products from the Ultrabithorax domain of the bithorax complex. EMBO J 7: 435–445.

Pabo, C. O. and R. T. Sauer. 1992. Transcription factors: structural families and principles of DNA recognition. Annu. Rev. Biochem. 61: 1053–1095.

Pagnier, J., J. G. Mears, O. Dunda-Belkhodja, K. E. Schaefer-Rego, C. Beldjord, R. L. Nagel, and D. Labie. 1984. Evidence of the multicentric origin of the hemoglobin S gene in Africa. Proc. Natl. Acad. Sci. USA 81: 1771–1773.

Papayannopoulou, T., T. H. Shepard, and G. Stamatoyannoupoulos.1983. Studies of hemoglobin expression in erythroid cells of early human fetuses using anti-γ- and anti-β-globin chain fluorescent antibodies, p.421–430. In G. Stamatoyannopoulos and A. W. Nienhuis (ed.), Globin Gene Expression and Hematopoietic Differentiation. Alan R. Liss, New York.

Perrine, S. P., B. A. Miller, D. V. Faller, R. A. Cohen, E. P. Vichinsky, D. Hurst, B. H. Lubin, and T. Papayannopoulou. 1989. Sodium butyrate enhances fetal globin gene expression in erythroid progenitors of patients with HbSS and β thalassemia. Blood 74: 454–459.

Perrine, S. P., B. A. Miller, M. F. Greene, R. A. Cohen, N. Cook, C. Shackleton, and D. V. Faller. 1987. Butyric acid analogues augment γ globin gene expression in neonatal erythroid progenitors. Biochem. Biophys. Res. Comm. 148: 694–700.

Perrine, R. P., M. E. Pembrey, S. Perrine, and F. Shoup. 1978. Natural history of sickle cell anemia in Saudi Arabs. A study of 270 subjects. Ann. Internal. Med. 88: 1–6.

Price, J. A., D. W. Bowden, J. T. Wright, M. J. Pettenati, and T. C. Hart. 1998. Identification of a mutation in Dlx3 associated with tricho-dento-osseous (TDO) syndrome. Hum. Mol. Gen. 7: 563–569.

Quinn, L. M., B. V. Johnson, J. Nicholl, G. R. Sutherland, and B. Kalionis. 1997. Isolation and identification of homeobox genes from human placenta including a novel member of the Distal-less family, Dlx4. Gene 187: 55–61.

Robinson, G. W. and K. Mahon. 1994. Differential and overlapping expression domains of Dlx-2 and Dlx-3 suggest distinct roles for Distal-less homeobox genes incraniofacial development. Mech. Dev. 48: 199–215.

Schechter, A. N., C. T. Noguchi and G. P. Rodgers. 1987. Sickle cell disease, p. 179–218. In G. Stamatoyannopoulos, A. W. Nienhuis, P. Leder, Majerus, P. W. (ed.), The Molecular Basis of Blood Diseases. Saunders, Philadelphia.

Shimamoto, T., S. Nakamura, J. Bollekens, F. H. Ruddle and K. Takeshita. 1997. Inhibition of Dlx-7 homeobox gene causes decreased expression of GATA-1 and c-myc genes and apoptosis. Proc. Natl. Acad. Sci. USA 94: 3245–3249.

Simeone, A., D. Acampora, M. Pannese, M. D'Esposito, A. Stornaiuolo, M. Gulisano, A. Mallamaci, K. Kastury, T. Druck, and K. Huebner. 1994. Cloning and characterization of two members of the vertebrate Dlx gene family. Proc. Natl. Acad. Sci. USA 91: 2250–54.

Stock, D. W., D. L. Ellies, Z. Zhao, M. Ekker, F. H. Ruddle, and K. M. Weiss. 1996. The evolution of the vertebrate Dlx family. Proc. Natl. Acad. Sci. USA 93: 10858–10863.

Tuan, D., W. Soloman, Q. Li, and I. M. London. 1985. The "β-like-globin" gene domain in human erythroid cells. Proc. Natl. Acad. Sci. USA 82: 6384–6388.

Vinson, C. R., K. L. LaMarco, P. F. Johnson, W. H. Landschulz, and S. L. McKnight. 1988. In situ detection of sequence-specific DNA binding activity specified by a recombinant bacteriophage. Genes & Devel. 2: 801–806.

Wu, S., Q. Lu, and A. L. Kriz. 1995. Multiple-sandwich, one-step hybridization of Northern and Southern blots. BioTechniques 18: 585–586.

Zeng, F.-y., G. P. Rodgers, S.-z. Huang, A. N. Schechter, M. Salamah, S. Perrine, and P. E. Berg. 1994. Sequence of the −530 region of the beta globin gene of sickle cell anemia patients with the Arabian haplotype. Human Mutation 3: 163–165.Chase M B, Haga S, Fu S, Davenport G, Morgan D, Mah A, Berg P E. Repression of the human β-globin gene by BP1, a new homeodomain protein. Submitted.

Levine M, Hoey T. Homeobox proteins as sequence-specific transcription factors. Cell 1988; 55: 537–540. van Oostveen J W, Biji J J, Raaphorst F M, Walbooners J J M, Meijer C J L M. The role of homeobox genes in normal hematopoiesis and hematological malignancies. Leukemia 1999; 13: 1675–1690. Look A T. Oncogenic transcription factors in the human acute leukemias. Science 1997; 278: 1059–1064.

Lu Q, Wright D D, Kamps M P. Fusion with E2A converts the Pbx1 homeodomain protein into a constitutive transcriptional activator in human leukemias carrying the t(1;19) translocation. Mol Cell Biol 1994; 14: 3938–3948.

Nakamura T, Yamazaki Y, Hatano Y, Miura I. NUP98 is fused to PMX1 homeobox gene in human acute myelogenous leukemia with chromosome translocation t(1;11) (q23;p15). Blood 1999; 94: 741–747.

Petrini M, Quaranta M T, Testa U, Samoggia P, Tritarelli E, Care A, Cianetti L, Valtieri M, Barletta C, Peschle C. Expression of selected human HOX genes in B/T acute lymphoid leukemia and interleukin-2/interleukin-1 β-stimulated natural killer lymphocytes. Blood 1992; 80: 185–193.

Hawley R G, Fong A Z C, Reis M D Zhang N, Lu M, Hawley T S. Transforming function of the HOX11/TCL3 homeobox gene. Cancer Res 1997; 57: 337–345.

Fu S, Strovel J W, Haga S B, Stamberg J, Berg P E. Mapping of a new homeobox gene, BP1, near its isoform DLX7 and characterization of their roles in repression of the beta globin gene. Am. J. Hum. Gen. 1998; 63:A181.

Pui C-H. Childhood leukemias. New Eng J Med 1995; 332: 1618–1630.

Karp J E. Acute leukemia: mechanisms of cell survival as targets for therapy. Int J Oncol 1997; 11: 657–674. Copelan E A, McGuire E A. The biology and treatment of acute lymphoblastic leukemia in adults. Blood 1995; 85: 1151–1168.

Tenen D G, Hromas R, Licht J D, Zhang D-E. Transcription factors, normal myeloid development and leukemia. *Blood* 1997; 90: 489–491.

Gewirtz A M, Calabretta B. A c-myb antisense oligodeoxynucleotide inhibits normal human hematopoiesis in vitro. *Science* 1988; 242: 1303–1306.

Guerrasio A, Saglio G, Rosso C, Alfarano A, Camaschella C, Lo Coco F, Biondi A, Ranbaldi A, Nicolis S, Ottolenghi S. Expression of GATA-1 mRNA in human myeloid leukemic cells. *Leukemia* 1994; 6: 1034–1038.

Crotta S, Nicolis S, Ronchi A, Ottolenghi S, Ruzzi L, Shimada Y, Migliaccio A R. Progressive inactivation of the expression of an erythroid transcriptional factor in GM- and G-CSF-dependent myeloid cell lines. *Nucl Acids Res* 1990; 18: 6863–6869.

Gonda T, Metcalf D. Expression of myb, myc and fos proto-oncogenes during the differentiation of a murine myeloid leukemia. *Nature* 1984; 310: 249–251.

Luscher B, Eisenman R N. New light on Myc and Myb. Part II. Myb. *Genes & Devel* 1990; 4: 2235–2241.

Raff T, van der Giet M, Endemann D, Wiederholt T, Paul M. Design and testing of β-actin primers for RT-PCR that do not co-amplify processed pseudogenes. *BioTechniques* 1997; 23: 456–460.

Majello B, Kenyon L C, Dalla-Favera R. Human c-myb protooncogene: nucleotide sequence of cDNA and organization of the genomic locus. *Proc Natl Acad Sci* 1986; 83: 9636–9640.

Tsai S F, Martin D I K, Zon L I, D'Andrea A D, Wong G G, Orkin S H. Cloning of the cDNA for the major DNA-binding protein of the erythroid lineage through expression in mammalian cells. *Nature* 1989; 339: 446–451.

Chen Q, Cheng J-T, Tsai L-H, Schneider N, Buchanan G, Carroll A, Crist W, Ozanne B, Siciliano M J, Baer R. The tal gene undergoes chromosome translocation in T cell leukemia and potentially encodes a helix-loop-helix protein. *EMBO J* 1990; 9: 415–424.

Bennett J M, Catovsky D, Daniel M T, Flandrin G, Galton D A G, Gralnick H R, Sultan C. Proposed revised criteria for the classification of the French-American-British Cooperative Group. *Ann Intern Med* 1985; 103: 620–625.

Baer M R, Stewart C C, Lawrence D, Arthur D C, Mrozek K, Strout M P, Davey F R, Schiffer C A, Bloomfield C D. Acute myeloid leukemia with 11q23 translocations: myelomonocytic immunophenotype by multiparameter flow cytometry. *Leukemia* 1998; 12: 317–325.

Taki T, Ohnishi H, Shinohara K, Sako M, Bessho F, Yanagisawa M, Hayashi Y. AF17q25, a putative septin family gene, fuses the MLL gene in acute myeloid leukemia with t(11;17)(q23;q25). *Cancer Res* 1999; 59: 4261–4265.

Osaka M, Rowley J D, Zeleznik-Le N J. MSF (MLL septin-like fusion), a fusion partner gene of MLL, in a therapy-related acute myeloid leukemia with a t(11;17) (q23;q25). *Proc Natl Acad Sci USA* 1999; 96: 6428–6433.

Yu B D, Hess J L, Horning S E, Brown G A J, Korsmeyer S. Altered Hox expression and segmental identity in M11-mutant mice. *Nature* 1995; 378: 505–508.

Wolff L, Koller R, Bies J, Nazarov V, Hoffman B, Amanullah A, Krall M, Mock B. Retroviral insertional mutagenesis in murine promonocytic leukemias: c-myb and Mml1. *Curr Topics Micro Immuno* 1996; 211: 191–199.

Shen W-F, Largman C, Lowney P, Corral J C, Detmer K, Hauser C A, Simonitch T A, Hack F M, Lawrence H J. Lineage-restricted expression of homeobox-containing genes in human hematopoetic cell lines. *Proc Natl Acad Sci USA* 1989; 86: 8536–8540.

Magli C M, Barba, P, Celetti A, De Vita G, Cillo, C, Boncinelli E. Coordinate regulation of HOX genes in human hematopoietic cells. *Proc Natl Acad Sci USA* 1991; 88: 6348–6352.

Mathews C H E, Detmer K, Boncinelli E, Lawrence H J, Largman C. Erythroid-restricted expression of homeobox genes of the human HOX2 locus. *Blood* 1991; 78: 2248–2252.

Celetti A, Barba P, Cillo C, Rotoli B, Boncinelli E, Magli M C. Characteristic patterns of HOX gene expression in different types of human leukemia. *Int J Cancer* 1993; 53: 237–244.

Lawrence H J, Sauvageau G, Ahmadi N, Lopez A R, LeBeau M M, Link M, Humphries K, Largman C. Stage- and lineage-specific expression of the HOXA10 homeobox gene in normal and leukemic hematopoietic cells. *Exp Hem* 1995; 23: 1160–1166.

Biji J J, van Oostveen J W, Walboomers J M M, Brink A T P, Vos W, Ossenkoppele G J, Meijer C J L M. Differentiation and cell-type-restricted expression of HOXC4, HOXC5 and HOXC6 in myeloid leukemias and normal myeloid cells. *Leukemia* 1998; 12: 1724–1732.

Kawagoe H, Humphries R K, Blair A, Sutherland H J, Hogge D E. Expression of HOX genes, HOX cofactors, and MLL in phenotypically and functionally defined subpopulations of leukemic and normal human hematopoietic cells. *Leukemia* 1999; 13: 687–698.

Salvati P D, Ranford P R, Ford J, Kees U R. HOX11 expression in pediatric acute lymphoblastic leukemia is associated with T-cell phenotype. *Oncogene* 1995; 11: 1333–1338.

Cuneo A, Mecucci C, Kerim S, Vandenberghe E, Dal Cin P, Van Orshoven A, Rodhain J, Bosly A, Michaux J L, Martiat P., Boogaerts M, Carli M G, Castoldi G, Van Den Berghe H. Multipotent stem cell involvement in megakaryoblastic leukemia: cytologic and cytogenetic evidence in 15 patients. *Blood* 1989; 74: 1781–1790.

Bonnet D, Dick J E. Human acute leukemia is organized as a hierarchy that originates from a primitive hematopoietic cell. *Nature Medicine* 1997; 3: 730–737.

Venditti A, Del Poeta G, Buccisano F, Tamburini A, Cox M C, Stasi R, Bruno A, Aronica G, Maffei L, Suppo G, Simone M D, Forte L, Cordero V, Postorino M, Tufilli V, Isacchi G, Masi M, Papa G, Amadori S. Minimally differentiated acute myeloid leukemia (AML-MO): Comparison of 25 cases with other French-American-British subtypes. *Blood* 1997; 89: 621–629.

Sauvageau G, Lansdorp P M, Eaves C J, Hogge D E, Dragowska W H, Reid D S, Largman C, Lawreence J, Humphries R K. Differential expression of homeobox genes in functionally distinct CD34+ subpopulations of human bone marrow cells. *Proc Natl Acad Sci USA* 1994; 91: 12223–12227. Differential expression of homeobox genes in functionally distinct CD34+ subpopulations of human bone marrow cells. *Proc Natl Acad Sci USA* 1994; 91: 12223–12227.

Bhatia M, Bonnet D, Murdoch B, Gan O I, Dick J E. A newly discovered class of human hematopoietic cells with SCID-repopulating activity. *Nature Med* 1998; 4: 1038–1045.

Goodell M A. CD34+ or CD34−: does it really matter? *Blood* 1999; 94: 2545–2547.

Sato T, Laver J H, Ogawa M. Reversible expression of CD34 by murine hematopoietic stem cells. *Blood* 1999; 94: 2548–2554.

Schiffer C A. Acute myeloid leukemia in adults, in Holland J F, Frei E., Bast R C, Kufe D W, Morton D L, Weichselbaum R R (eds): Cancer Medicine. Philadelphia, Pa. Lea & Febiger, 1997. Scott M P, Tamkun J W, Hartzel 111 G W. The structure and function of the homeodomain. Biochem Biophys Acta 989: 25, 1989.

Bennett J M, Catovsky D, Daniel M T, Flandrin G, Galton D A G, Gralnick H R, Sultan C. Proposed revised criteria for the classification of the French-American-British Cooperative Group. Ann Intern Med 103: 103, 1985.

Luscher B, Eisenman R N. New light on Myc and Myb. Part II. Myb. Genes & Devel 4: 2235, 1990.

Crotta S, Nicolis S, Ronchi A, Ottolenghi S, Ruzzi L, Shimada Y, Migliaccio A R. Progressive inactivation of the expression of an erythroid transcriptional factor in GM- and G-CSF dependent myeloid cell lines. Nucl Acids Res 18: 6863, 1990.

Romeo P-H, Prandini M-H, Joulin V, Mignotte V, Prenant M, Vainchenker W, Marguerie G, Uzan G. Megakaryocytic and erythrocytic lineages share specific transcription factors. Nature 344: 447, 1990.

Martin D I K, Orkin S H: Transcriptional activation and DNA binding by the erythroid factor GM1/NF-E1/ERYF1. Genes Dev 4: 1886, 1990.

Perkins A, Kongsuwan K, Visvader J, Adams J M, Cory S: Homeobox gene expression plus autocrine growth factor production elicits myeloid leukemia. Proc Natl Acad Sci USA 87: 8398, 1990.

Lawrence H J, Sauvageau G, Ahmadi N, Lopez A R, LeBeau M M, Link M, Humphries K, Largman C: Stage- and lineage-specific expression of the HOXA10 homeobox gene in normal and leukemic hematopoietic cells. Exp Hem 23: 1160, 1995.

Lawrence H. J., Sauvageau G, Humphries R. K., Largman C: The role of HOX homeobox genes in normal and leukemic hematopoiesis. Stem Cells 14: 281, 1996.

Thorsteinsdottir U, Sauvageau G, Humphries R K: HOX homeobox genes as regulators of normal and leukemic hematopoesis. Aplastic Anemia and Stem Cell Biol 11: 1221, 1997.

Borrow J, Shearman A. M., Stanton Jr. V. P., Becher R, Collins T, Williams A. J., Dube I, Katz F, Kwong Y L, Morris C, Ohyashiki K, Toyama K, Rowley J, Housman D E: The t(7;11) (p15;p15) translocation in acute myeloid leukaemia fuses the genes for nucleoporin NUP98 and class I homeoprotein HOXA9. Nature Genetics 12: 159, 1996.

Nakamura T, Largaespada D A, Lee M P, Johnson L A, Ohyashiki K, Toyama K, Chen S J, Willman C L, Chen l-M, Feinberg A P, Jenkins N A, Copeland N G, Shaughnessy Jr J D: Fusion of the nucleoporin gene NUP98 to HOXA9 by the chromosome translocation t(7;11) (p15;p15) in human myeloid leukaemia. Nature Genetics 12: 154, 1996.

Shimamoto T, Ohyashiki K, Ohyashiki J H, Kawakubo K, Fujimura T, Iwama H, Nakazawa S, Toyama K: The expression pattern of erythrocyte/megakaryocyte-related transcription factors GATA-1 and the stem cell leukemia gene correlates with hematopoietic differentiation and is associated with outcome of acute myeloid leukemia. Blood 86: 3173, 1995.

Komatsu N, Kirito K, Izuma T, Eguchi M, Miura Y: GATA-1 and erythropoietin receptor genes are highly expressed in erythroleukemia. Exp Hem 26: 1148, 1998.

Thompson M A, Ramsay R G: Myb: an old oncoprotein with new roles. Bioessays 17: 341, 1995.

Bash, R. O., Hall, S., Timmons, C. F., Crist, W. M., Amylone, M., and Smith, and Baer, R. (1995) Does activation of the TAL1 gene occur in a majority of patients with T cell acute lymphoblastic leukemia? A Pediatric Oncology Group Study. Blood 86: 666–676.

Brown, L., Cheng, J-T., Chen, Q., Siciliano, M. J., Crist, W., Buchanan, G. and Baer, R. (1990) Site-specific recombination of the tar-1 gene is a common occurrence in human T cell leukemia. EMBO J 9: 3343–3351.

Bernard, O., Lecointe, N., Jonveaux, p., Souyr, M., Mauchauffe, M., Berger, R., Larsen, C. J. and Mathieu-Mahul, D. (1991) Two site-specific deletions and t(1;14) translocation restricted to human T-cell acute leukemias disrupt the 5' part of the tar-1 gene. Oncogene 6: 1477–1488.

Aplan, P. D., Lombardi, D. P., Reaman, G., Sather, H., Hammond, G. and Kirsch, I. R. (1992), Involvement of the putative hemotopoletic transcription factor SCL in T cell acute Iymphoblastic leukemia. Blood 79: 1327–1333.

Begley, C. G., Aplan, P. D., Denning, S. M., Haynes, B. F., Waldmann, T. A. and Kirsch, I. R. (1989) The gene SCL is expressed during early hematopoiesis and encodes a differentiation-related DNA-binding motif. Proc. Natl. Acad. Sci. 86: 10128–10132.

Visvader, J., Begley, C. G. and Adams, J. M. (1990) Differential expression of the LYL, SCL and E2A helix-loop-helix genes within the hemopoletic system. Oncogene 6: 187–194.

Civin Cl, Strauss L C, Brovall C, Fackler M J, Schwartz J F, Shaper J H: Antigenic analysis of hematopoiesis. ill. A hematopoietic progenitor cell surface antigen defined by a monoclonal antibody raised against KG-1a cells. J Immunol 133: 157, 1984.

Elwood, N. J., Cook, W. D., Metcalf, D. and Begley, C. G. (1993) SCL, the gene implicated in human T-cell leukemia, is oncogenic in a murine T-lymphocyte cell line. Oncogene 8: 3093–3101.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

The invention claimed is:

1. An isolated DNA having SEQ ID NO: 1, encoding BP1.
2. A vector comprising the isolated DNA of claim 1.
3. An isolated host cell transformed with the vector of claim 2.
4. An isolated host cell according to claim 3, wherein said host cell is a eukaryotic host cell.
5. A composition comprising a set of PCR primers that amplifies a unique DNA molecule from a substrate of cDNA of mRNA that encodes for BP1 of SEQ ID NO: 1 wherein the set of PCR primers comprises the oligonucleotides of SEQ ID NO: 8 and SEQ ID NO: 9.
6. A composition comprising a set of PCR primers that amplifies a unique DNA molecule from a substrate of cDNA of mRNA that encodes for BP1 of SEQ ID NO: 1 wherein the set of PCR primers comprises the oligonucleotides of SEQ ID NOs: 10 and SEQ ID NO: 11.

* * * * *